(12) United States Patent
Bissinger et al.

(10) Patent No.: US 10,149,481 B2
(45) Date of Patent: Dec. 11, 2018

(54) ARTHROPOD CONTROL COMPOSITIONS AND METHODS

(71) Applicant: Tyratech, Inc., Morrisville, NC (US)

(72) Inventors: Brooke Bissinger, Morrisville, NC (US); Keith Kennedy, Morrisville, NC (US); Jason Schmidt, Morrisville, NC (US)

(73) Assignee: TYRATECH, INC., Morrisville, NC (US)

( * ) Notice: Subject to any disclaimer, the term of this patent is extended or adjusted under 35 U.S.C. 154(b) by 542 days.

(21) Appl. No.: 14/436,827

(22) PCT Filed: Oct. 18, 2013

(86) PCT No.: PCT/US2013/065773
§ 371 (c)(1),
(2) Date: Apr. 17, 2015

(87) PCT Pub. No.: WO2014/063109
PCT Pub. Date: Apr. 24, 2014

(65) Prior Publication Data
US 2016/0165899 A1 Jun. 16, 2016

Related U.S. Application Data

(60) Provisional application No. 61/716,360, filed on Oct. 19, 2012, provisional application No. 61/789,424, filed on Mar. 15, 2013.

(51) Int. Cl.
| | |
|---|---|
| *A61K 36/53* | (2006.01) |
| *A61K 36/00* | (2006.01) |
| *A61K 36/534* | (2006.01) |
| *A01N 65/22* | (2009.01) |
| *A01N 37/02* | (2006.01) |
| *A01N 37/40* | (2006.01) |
| *A01N 49/00* | (2006.01) |
| *A61Q 17/02* | (2006.01) |
| *A61K 8/31* | (2006.01) |
| *A61K 8/34* | (2006.01) |
| *A61K 8/36* | (2006.01) |
| *A01N 31/02* | (2006.01) |
| *A01N 35/04* | (2006.01) |
| *A01N 37/36* | (2006.01) |
| *A01N 43/16* | (2006.01) |

(52) U.S. Cl.
CPC ............ *A01N 65/22* (2013.01); *A01N 31/02* (2013.01); *A01N 35/04* (2013.01); *A01N 37/02* (2013.01); *A01N 37/36* (2013.01); *A01N 37/40* (2013.01); *A01N 43/16* (2013.01); *A01N 49/00* (2013.01); *A61K 8/31* (2013.01); *A61K 8/342* (2013.01); *A61K 8/361* (2013.01); *A61Q 17/02* (2013.01)

(58) Field of Classification Search
None
See application file for complete search history.

(56) References Cited

U.S. PATENT DOCUMENTS

| | | |
|---|---|---|
| 5,227,406 A | 7/1993 | Beldock et al. |
| 5,364,626 A | 11/1994 | Hasegawa et al. |
| 6,143,288 A | 11/2000 | Warren et al. |
| 7,541,155 B2 | 6/2009 | Enan |
| 7,622,269 B2 | 11/2009 | Enan |
| 8,481,063 B2 | 7/2013 | Bencsits |
| 8,501,247 B2 | 8/2013 | Enan et al. |
| 8,507,013 B2 | 8/2013 | Enan |
| 8,685,471 B2 | 4/2014 | Enan |
| 8,691,256 B2 | 4/2014 | Enan |
| 8,734,869 B2 | 5/2014 | Enan |
| 8,771,718 B2 | 7/2014 | Scialdone et al. |
| 8,834,908 B2 | 9/2014 | Jones |
| 8,865,230 B2 | 10/2014 | Enan |
| 8,993,004 B2 | 3/2015 | Lindner et al. |
| 9,492,490 B1 | 11/2016 | Enan |
| 2003/0198659 A1* | 10/2003 | Hoffmann ............ A01N 25/34 424/411 |
| 2006/0263403 A1 | 11/2006 | Enan |
| 2008/0047312 A1 | 2/2008 | Hill et al. |
| 2008/0069785 A1 | 3/2008 | Jones |
| 2008/0075796 A1 | 3/2008 | Enan |
| 2008/0145462 A1 | 6/2008 | Enan |
| 2009/0099135 A1 | 4/2009 | Enan |
| 2009/0232918 A1 | 9/2009 | Enan |
| 2010/0260873 A1* | 10/2010 | Lindner ................. A01N 25/04 424/747 |

(Continued)

FOREIGN PATENT DOCUMENTS

| | | |
|---|---|---|
| CN | 101297644 A | 11/2008 |
| WO | WO 00/05948 A1 | 2/2000 |
| WO | WO 2010/117740 A2 | 10/2010 |

OTHER PUBLICATIONS

U.S. Appl. No. 15/286,110, filed Oct. 5, 2016.
Nentwig, G., "Use of repellents as prophylactic agents", Parasitol Res, 2003, vol. 90, pp. S40-S48.
Bissinger et al., "Efficacy of the new repellent BioUD against three species of ixodid ticks", Exp Appl Acarol, 2009, vol. 48, pp. 239-250.
Bissinger et al., "Novel field assays and the comparative repellency of BioUD®, DEET and permethrin against Amblyomma americanum", Medical and Veterinary Entomology, 2011, vol. 25, pp. 217-226.
Carroll et al., "Twelve-hour duration testing of cream formulations of three repellents against Amblyomma americanum", Medical and Veterinary Entomology, 2008, vol. 22, pp. 144-151.

(Continued)

*Primary Examiner* — Christopher R Tate
*Assistant Examiner* — Randall Winston
(74) *Attorney, Agent, or Firm* — K&L Gates LLP

(57) ABSTRACT

The present invention relates to compositions and methods related to controlling arthropods. Embodiments of the invention include compositions for controlling an arthropod, which can include one or more plant essential oils and methods for using these compositions. The plant essential oils, when combined, can have a synergistic effect.

17 Claims, 16 Drawing Sheets

(56) References Cited

U.S. PATENT DOCUMENTS

| | | |
|---|---|---|
| 2011/0003317 A1 | 1/2011 | Enan |
| 2011/0008471 A1 | 1/2011 | Enan |
| 2011/0135764 A1* | 6/2011 | Enan ............... A01N 65/00 424/745 |
| 2011/0171135 A1 | 7/2011 | Enan |
| 2014/0377385 A1 | 12/2014 | Enan |
| 2015/0087516 A1 | 3/2015 | Enan |
| 2015/0150838 A1 | 6/2015 | Enan et al. |
| 2015/0201615 A1 | 7/2015 | Schmidt et al. |
| 2016/0029625 A1 | 2/2016 | Kennedy et al. |

OTHER PUBLICATIONS

Schmidt, C., "Outsmarting Olfaction the Next Generation of Mosquito Repellents", Environmental Health Perspectives, Jul. 2005, vol. 113, No. 7, pp. A468-A471.

Kimps et al., "First report of the repellency of 2-tridecanone against ticks", Medical and Veterinary Entomology, 2011, vol. 25, pp. 202-208.

Fradin et al., "Comparative Efficacy of Insect Repellents Against Mosquito Bites", N Engl J Med, Jul. 4, 2002, vol. 347, No. 1, pp. 13-18.

"Product Performance Test Guidelines OPPTS 810.3700: Insect Repellents to be Applied to Human SkinUnited States Environmental Protection Agency", Office of Chemical Safety and Pollution Prevention (7101), EPA 712-C-10-001, Jul. 7, 2010, 41 pages.

Aquino et al., "West Nile Virus in British Columbia", Emerging Infectious Diseases, www.cdc.gov/eid, Aug. 2004, vol. 10, No. 8, pp. 1499-1501.

Salafsky et al., "Short Report: Study on the Efficacy of a New Long-Acting Formulation of N, N-Diethyl-m-Toluamide (Deet) for the Prevention of Tick Attachment", Am. J. Trop. Med. Hyg.,2000, vol. 62, No. 2, pp. 169-172.

Hamm et al., "A Cline in Frequency of Autosomal Males Is Not Associated with Insecticide Resistance in House Fly (Diptera: Muscidae)", J. Econ. Entomol., 2005, vol. 98, No. 1, pp. 171-176.

Goodyer et al., "Short Report: The Safety and Toxicity of Insect Repellents", Am. J. Trop. Med. Hyg., 1998, vol. 59, No. 2, pp. 323-324.

Thomas et al., "Comparison of Three Sampling Methods for Estimating Adult Stable Fly (Diptera: Muscidae) Populations", Environ, Entornol., 1989, vol. 18, No. 3, pp. 513-520.

Barnard, D., "Repellency of Essential Oils to Mosquitoes (Diptera: Culicidae)", J. Med. Entomol., Sep. 1999, vol. 36, No. 5, pp. 625-629.

Gubler et al., "Dengue/Dengue Hemorrhagic Fever: The Emergence of a Global Health Problem", Emerging Infectious Diseases, 1995, vol. 1, No. 2, pp. 55-57.

Clem et al., "Insect Repellent (N,N-Diethyl-m-toluamide) Cardiovascular Toxicity in an Adult", Ann Pharmacother, Mar. 1993, vol. 27, pp. 289-293.

DEET, Showers, and Tick Checks Can Stop Ticks, Centers for Disease Control and Prevention, 2012, http://www.cdc.gov/Features/StopTicks/, Jun. 4, 2012, 2 pages.

Schulze et al., "Geographical Distribution and Prevalence of Selected Borrelia, Ehrlichia and Rickettsia Infections in Amblyomma Americanum (AcariL Ixodidae) in New Jersey", Journal of the American Mosquito Control Association, 2011, vol. 27, No. 3, pp. 236-244.

Frances, S., "Efficacy and Safety of Repellents Containing Deet", Insect Repellents: Principles, Methods, and Uses, Taylor & Francis Group, LLC, 2007, pp. 311-325.

Frances, S., "Picaridin", Insect Repellents: Principles, Methods, and Uses, Taylor & Francis Group, LLC, 2007, pp. 337-340.

Strickman, D., "PMD (p-Menthane-3,8-Diol) and Quwenling", Insect Repellents: Principles, Methods, and Uses, Taylor & Francis Group, LLC, 2007, pp. 347-351.

Xue et al., "Commercially Available Insect Repellents and Criteria for Their Use", Insect Repellents: Principles, Methods, and Uses, Taylor & Francis Group, LLC, 2007, pp. 405-415.

Moore et al., "History of Insect Repellents", Insect Repellents: Principles, Methods, and Uses, Taylor & Francis Group, LLC, 2007, pp. 3-29.

Shulaev et al., "Airborne signalling by methyl salicylate in plant pathogen resistance", Nature, vol. 382, Feb. 1997, pp. 718-721.

Masters et al., "STARI, or Masters Disease: Lone Star Tick—Vectored Lyme-like Illness", Infect Dis Clin N Am, 2008, vol. 22, pp. 361-376.

Marten et al., "A State-by-State Survey of Ticks Recorded From Humans in the United States", Journal of Vector Ecology, 2000, vol. 25, No. 1, pp. 102-113.

James et al., "Field-Testing of Methyl Salicylate for Recruitment and Retention of Beneficial Insects in Grapes and Hops", Journal of Chemical Ecology, Aug. 2004, vol. 30, No. 8, pp. 1613-1628.

Robertson et al., "Yellow Fever, A Decade of Reemergence", JAMA, Oct. 9, 1996, vol. 276, No. 14, pp. 1157-1162.

McMullan et al., "A New Phlebovirus Associated with Severe Febrile Illness in Missouri", The New England Journal of Medicine, 2012, vol. 367, pp. 834-841.

EPA Product Performance Test Guidelines Insect Repellents to be Applied to Human Skin, United States Environmental Protection Agency, Sep. 23, 2008, 45 pages.

Johnson et al., Chapter 12, Synthetic Fatty Acids, "Fatty Acids in Industry, Processes, Properties, Derivatives, Applications", Marcel Dekker, Inc., 1989, pp. 277-326.

Slaff, Mark and C. S. Apperson, "A Key to the Mosquitoes of North Carolina and the Mid-Atlantic States", Publication AG-412, Agricultural Extension Service, North Carolina State University, 1989, Raleigh, N. C., 46 pages.

Foster et al., "Chapter 14, Mosquitoes (Culicidae)", Medical and Veterinary Entomology, Elsevier, Inc., 2009, pp. 207-259.

Nicholson et al., "Chapter 26, Ticks (Ixodida)", Medical and Veterinary Entomology, Elsevier, Inc., 2009, pp. 493-527.

Base SAS® 9.1.3 Procedures Guide, Second Edition, SAS Publishing, SAS Institute Inc., Cary, NC, 2006, 78 pages. (Part 1).

Base SAS® 9.1.3 Procedures Guide, Second Edition, SAS Publishing, SAS Institute Inc., Cary, NC, 2006, 144 pages. (Part 2).

Sonenshine, Daniel E., Biology of Ticks, vol. 2, Oxford University Press, New York, 1993, pp. 4-11, 42-47, 107-109, 157-158, 194-195, 255-256 and 320.

Veltri et al., Retrospective Analysis of Calls to Poison Control Centers Resulting from Exposure to the Insect Repellent N,N-Diethyl-M-Toluamide (DEET) from 1985-1989, Clinical Toxicology, 32, 1, 1994, pp. 1-16.

Sonenshine, Daniel E., Biology of Ticks, vol. 1, Oxford University Press, New York, 1991, pp. 64-66.

* cited by examiner

ARTHROPOD CONTROL COMPOSITIONS AND METHODS

CROSS-REFERENCE TO RELATED APPLICATIONS

The present application is a U.S. National Stage entry under 35 U.S.C. § 371 of International Application No. PCT/US2013/065773, filed on Oct. 18, 2013, designating the United States of America and published in English on Apr. 24, 2014, which in turn claims priority to U.S. Provisional Application No. 61/716,360, filed on Oct. 19, 2012 and U.S. Provisional Application No. 61/789,424, filed Mar. 15, 2013, the entire texts whereof are incorporated by reference into the present application.

FIELD OF THE INVENTION

The invention disclosed herein generally relates to compositions and methods related to controlling arthropods.

BACKGROUND

Arthropods are invertebrate animals with jointed limbs, a segmented body, and an exoskeleton. They belong to the phylum Arthropoda and include, but are not limited to arachnids, crustaceans, and insects.

Mosquitoes are considered the most dangerous animal in the world because of the number of disease organisms they can vector and the seriousness of these diseases to human and animal health (Schmidt 2005). *Aedes aegypti* is the principle vector of the viruses that cause dengue and yellow fevers (Gubler and Clark 1995, Robertson et al. 1996). *Anopheles quadrimaculatus* is the North American vector of the human malaria parasite (Foster and Walker 2009). *Culex quinquefasciatus* vectors St. Louis encephalitis and West Nile flaviviruses and filarial worms (Foster and Walker 2009). Personal repellents, applied to the skin or clothing can provide protection from mosquitoes and other biting arthropods. The gold standard insect repellent for the past 55 years is deet (N,N-diethyl-3-methylbenzamide). Deet provides good repellency against many mosquito species (Fradin and Day 2002, Frances 2007a) but has been criticized for its odor and skin feel and the fact that it is a plasticizer. Additionally, some incidences of toxicity have been reported (Clem et al. 1993, Veltri et al. 1994, Goodyear and Behrens 1998). Although the number of confirmed negative reports of deet toxicity is extremely small compared to the number of people who use deet, a portion of the population chooses to avoid products containing deet, thereby putting them at risk for mosquito-vectored disease.

Ticks are ectoparasitic obligate blood-feeders and important vectors of human and animal pathogens (Sonenshine 1993). Ticks pose serious concerns for humans, both in the number and range of disease organisms that they can vector and in localized allergic reactions at the bite site. Two tick species, the American dog tick, *Dermacentor variabilis* the lone star tick, *Amblyomma americanum*, are commonly found attached to people in the southern and eastern U.S. (Merten and Durden 2000). *Dermacentor variabilis* is the primary vector of *Rickettsia rickettsii*, the causative agent of Rocky Mountain Spotted Fever, in the eastern U.S. *Amblyomma americanum* is an aggressive tick that is a carrier of a number of organisms that can cause disease in humans including *Ehrlichia chaffeensis*, *E. ewingii*, and *Rickettsia amblyommi* (Schulze et al. 2011) and has been implicated as the vector of the novel phlebovirus, Heartland virus (Mc-Mullan et al. 2012). *Amblyomma americanum* also vectors Southern Tick Associated Rash Illness (STARI), which causes symptoms similar to Lyme disease, but whose etiological agent has yet to be conclusively identified (Masters et al. 2008). A third important tick species in the U.S. is the black-legged tick, *Ixodes scapularis*. This tick is the vector of the Lyme disease spirochete, *Borrelia burgdorferi* in eastern North America and the protozoans that cause human babesiosis (Nicholson et al. 2009). A fourth tick of importance is the brown dog tick, *Rhipicephalus sanguineus*. This tick exhibits a cosmopolitan distribution and is primarily a canine ectoparasite but also bites humans, can vector *R. rickettsii*, and can infest households in large numbers (Nicholson et al. 2009).

Bed bugs are parasitic insects of the cimicid family that feed on the blood of a host. *Cimex lectularius*, is the most common bed bug; it prefers to feed on human blood. Other *Cimex* species are specialized to other animals, e.g., bat bugs, *C. pipistrelli* (Europe), *C. pilosellus* (western US), and *C. adjunctus* (entire eastern US). A number of adverse health effects may result from bed bug bites, including skin rashes, blisters, psychological effects, and allergic symptoms. Adult bed bugs are light brown to reddish-brown, flattened, oval-shaped and have no hind wings. Like other parasites, bed bugs are attracted to their hosts by host cues—primarily carbon dioxide, secondarily by warmth, and also by certain chemicals. Bed bug infestations have been on the rise in the past decade. Resistance to traditional chemical pesticide treatments has also increased, making eradication even more difficult.

Fleas are insects from the order Siphonaptera. They are wingless, external parasites, that feed on the blood of a host. Fleas attack a wide variety of warm-blooded vertebrates including dogs, cats, humans, chickens, rabbits, squirrels, rats, ferrets, and mice. Flea bites can result in skin irritation and allergic reactions. Fleas are vectors for many viral, bacterial, and rickettsial diseases in humans and other animals. Notably, fleas were in part responsible for the bubonic plague epidemic by transmitting bacteria between rodents and humans. Resistance to traditional chemical pesticide treatments has also increased, making eradication even more difficult.

Flies are insects of the order Diptera. They have a pair of wings on the mesothorax. Flies are not only a nuisance but also are vectors of disease transmission. Some diseases transmitted by flies include typhoid, cholera and dysentery salmonella, anthrax, and tuberculosis.

Personal repellents are a key protection measure against arthropods such as mosquitoes ticks and provide a line of defense against the diseases that they may transmit. In addition to efficacy, a number of factors influence the use rate of personal repellents including safety (whether actual or perceived) and aesthetics such as skin feel and odor. There are many commercially available mosquito repellents; however, only four active ingredients are recommended for use in the U.S. by the CDC: deet, IR3535, Picaridin, and PMD. Deet has been shown in many studies to exhibit good repellency against numerous mosquito species. Although deet has been used for decades with relatively few reports of toxicity, the belief that deet is a health and environmental hazard still exists for some people (Aquino et al. 2004). IR3535 and Picaridin are two alternatives to deet that exhibit good aesthetic characteristics and low mammalian toxicity (Nentwig 2003, Frances 2007b, Moore and Debboun 2007); however, both are registered pesticides with the Environmental Protection Agency (EPA). PMD exhibits low rat oral and rabbit dermal toxicity, but is exceptionally irritating to the eyes and can cause irreversible eye damage (Strickman 2007). Current recommendations by the U.S. Centers for Disease Control and Prevention (2012) for prevention of tick bites are the use of a repellent containing ≥20% deet (N, N-diethyl-m-toluamide) on skin or the toxicant permethrin on clothing.

Formulation can play a critical role in extending repellent efficacy. For example, a liposomal formulation of deet provided complete protection on treated rabbits against attachment of adult *D. variabilis* and *A. americanum* ticks for 72 h compared to no protection by a standard formulation of deet (Salafsky et al. 2000). In another study, a polymer formulation of deet and cream formulations of Picaridin and SS220 provided almost complete repellency to nymphal *A. americanum* for 12 h (Carroll et al. 2008). The plant-derived repellent, unformulated 2-undecanone provided 74% repellency against *D. variabilis* 2 h after application (Kimps et al. 2011) compared to 98% repellency from 3-3.5 h after application when formulated in the product BioUD® (Bissinger et al. 2009). Most published research has focused on repellent active ingredient identification rather than formulation and formulation chemistry is often a guarded secret of private industries (Bissinger and Roe 2010).

A number of plant-based repellents are available commercially; in many cases because of their rapid registration process under the US EPA's FIFRA section 25(b), which provides exemption from federal registration for specific ingredients that are deemed demonstrably safe for their intended use. Many of the ingredients on the 25(b) list are highly volatile compounds, causing them to provide only short-term repellent duration. Increasing the concentration of active ingredient can lengthen the duration of repellency; however, many essential oils are irritating to the skin above a certain concentration (Barnard 1999). Additionally, the aesthetics (e.g., odor, appearance, tactile, residual odor, discoloration, etc.) of many plant-based repellents are poor. Moreover, most repellents are developed for use against mosquitoes rather than arthropods in general (e.g. ticks), making efficacy data on arthropod repellency less available (Bissinger and Roe 2010). Therefore, there is a need for a broad-spectrum arthropod repellent that provides a high level of repellency for an extended amount of time while simultaneously exhibiting desirable aesthetics, such as pleasant odor and skin feel.

One advantage of the present compositions used in the methods of the present invention is that compositions can be produced containing only ingredients exempt from EPA registration by virtue of their appearance on the FIFRA 25(b) list or Class 4(a) inert ingredient list making the composition completely safe for use, and potentially eligible for classification as an organic pest control agent.

DETAILED DESCRIPTION OF THE INVENTION

Figure 1:
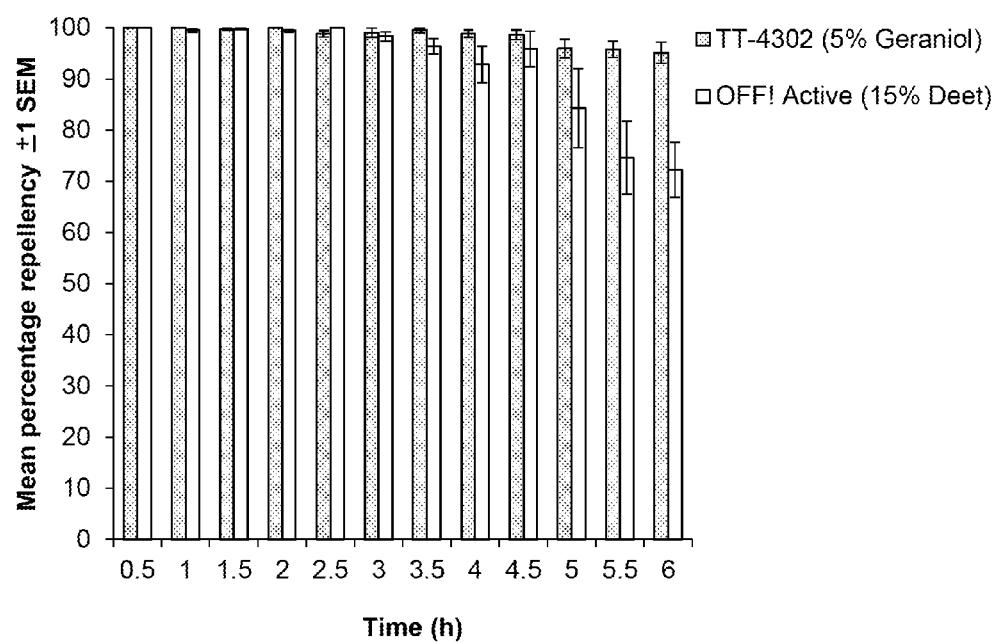
FIG. 1 shows the mean percentage repellency (±1 SEM) of TT-4302 and 15% deet against *Anopheles quadrimaculatus* in arm-in-cage studies (n=4) human volunteers per treatment).
Figure 2:
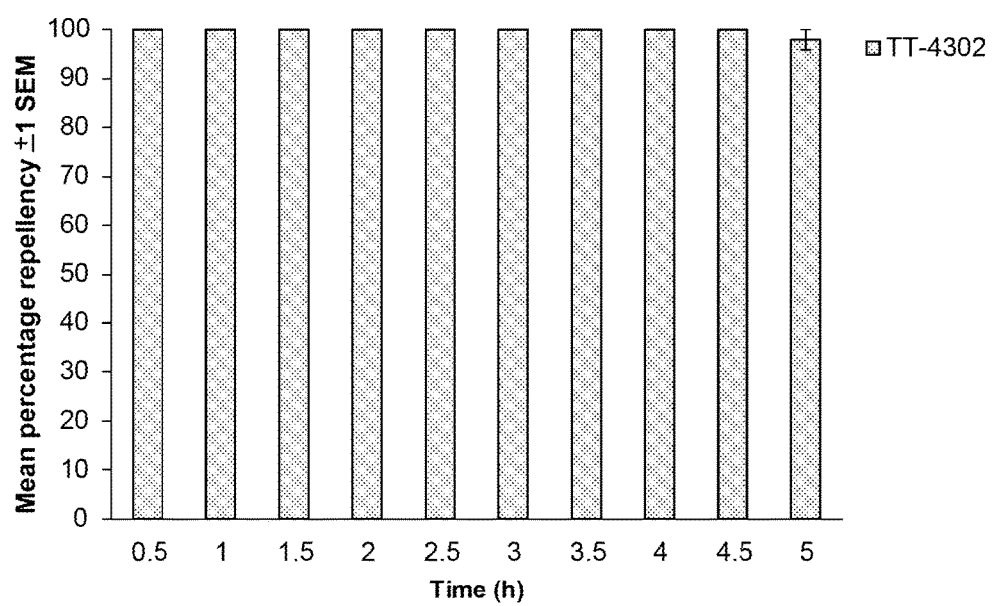
FIG. 2 shows the mean percentage repellency (±1 SEM) of TT-4302 against *Culex quinquefasciatus* in arm-in-cage studies (n=4 human volunteers per treatment).

Unless otherwise noted, terms are to be understood according to conventional usage by those of ordinary skill in the relevant art.

The present invention relates to compositions and methods related to controlling arthropods.

The compositions and methods of the invention can used to control any type of arthropod, such as an insect. Exemplary arthropods that can be controlled include but are not limited to beetles, cockroaches, flies, ants, larvae, bees, lice, fleas, mosquitoes, moths, and the like. Exemplary arthropod orders can include but are not limited to orders Acari, Anoplura, Araneae, Blattodea, Coleoptera, Collembola, Diptera, Grylloptera, Hemiptera, Heteroptera, Homoptera, Hymenoptera, Isopoda, Isoptera, Lepidoptera, Mantodea, Mallophaga, Neuroptera, Odonata, Orthoptera, Psocoptera, Siphonaptera, Symphyla, Thysanura, and Thysanoptera and the like.

Embodiments of the invention include compositions for controlling an arthropod, which can include one or more plant essential oils and methods for using these compositions. The plant essential oils, when combined, can have a synergistic effect. The compositions also can include a fixed oil, which is typically a non-volatile non-scented plant oil. Additionally, in some embodiments, these compositions can be made up of generally regarded as safe (GRAS) compounds.

For purposes of simplicity, the term "arthropod" shall be used in this application; however, it should be understood that the term "arthropod" refers, not only to insects, but also to mites, spiders, ticks, arachnoids, arachnids, larvae, parasites, and like invertebrates. Also for purposes of this application, the term "arthropod control" shall refer to having a repellent effect, a pesticidal effect, or both.

"Repellent effect" is an effect wherein more arthropods are repelled away from a host or area that has been treated with the composition than a control host or area that has not been treated with the composition. In some embodiments, repellent effect is an effect wherein at least about 50% of arthropods are repelled away from a host or area that has been treated with the composition. In some embodiments, repellent effect is an effect wherein at least about 75% of arthropods are repelled away from a host or area that has been treated with the composition. In some embodiments, repellent effect is an effect wherein at least about 90% of arthropods are repelled away from a host or area that has been treated with the composition. In some embodiments, repellent effect is an effect wherein at least about 95% of arthropods are repelled away from a host or area that has been treated with the composition.

"Pesticidal effect" is an effect wherein treatment with a composition causes at least about 1% of the arthropods to die. In this regard, an LC1 to LC100 (lethal concentration) or an LD1 to LD100 (lethal dose) of a composition will cause a pesticidal effect. In some embodiments, the pesticidal effect is an effect wherein treatment with a composition causes at least about 5% of the exposed arthropods to die.

In some embodiments, the pesticidal effect is an effect wherein treatment with a composition causes at least about 10% of the exposed arthropods to die. In some embodiments, the pesticidal effect is an effect wherein treatment with a composition causes at least about 25% of the arthropods to die. In some embodiments the pesticidal effect is an effect wherein treatment with a composition causes at least about 50% of the exposed arthropods to die. In some embodiments the pesticidal effect is an effect wherein treatment with a composition causes at least about 75% of the exposed arthropods to die. In some embodiments the pesticidal effect is an effect wherein treatment with a composition causes at least about 90% of the exposed arthropods to die.

In some embodiments of the invention, treatment with compositions of the invention will result in a knockdown of the arthropod occurring within a few seconds to a few minutes. "Knockdown" is an effect wherein treatment with a composition causes at least about 1% of the exposed arthropods to display reduced mobility. In some embodiments, the knockdown is an effect wherein treatment with a composition causes at least about 50% of the exposed arthropods to display reduced mobility.

The compositions of the present invention can be used to control arthropods by either treating a host directly, or treating an area in which the host will be located, for example, an indoor living space, outdoor patio or garden. For purposes of this application, host is defined as a plant, human, mammal, or other animal.

Treatment can include use of an oil-based formulation, a water-based formulation, an alcohol-based formulation, a residual formulation, and the like. In some embodiments, combinations of formulations can be employed to achieve the benefits of different formulation types.

Embodiments of the invention are directed to compositions for controlling arthropods and methods for using these compositions. In some embodiments, the compositions can include compounds that are generally regarded as safe (GRAS compounds). In some embodiments, the compositions can include compounds of a plant origin, such as plant essential oils or monoterpenoids of plant essential oils. In some embodiments, the compositions include two or more compounds. In some embodiments, the compositions can include any of the following oils, or mixtures thereof:

Methyl salicylate, also known as *betula* oil. Methyl salicylate is a major component of oil of wintergreen and is sometimes referred to interchangeably with oil of wintergreen. It is a natural product of many species of plants, is the methyl ester of salicylic acid, and can be produced chemically from the condensation reaction of salicylic acid and methanol. Some of the plants producing it are called wintergreens, hence the common name. Methyl salicylate can be used by plants as a pheromone to warn other plants of pathogens (Shulaev, et al. (Feb. 20, 1997) Nature 385: 718-721). The release of methyl salicylate can also function as an exopheromone aid in the recruitment of beneficial insects to kill the herbivorous insects (James, et al. (August 2004) J. Chem. Ecol. 30(8): 1613-1628). Numerous plants produce methyl salicylate including species of the family Pyrolaceae and of the genera *Gaultheria* and *Betula*. It is noted that, where a given blend or formulation or other composition is disclosed herein as containing wintergreen oil, an alternative embodiment, containing methyl salicylate in place of wintergreen oil, is also contemplated. Likewise, where a blend or formulation of other composition includes methyl salicylate, an alternative embodiment, containing wintergreen oil, is also contemplated.

Thyme Oil is a natural product that can be extracted from certain plants, including species from the Labiatae family; for example, thyme oil can be obtained from *Thymus vulgaris* (also known as, *T. ilerdensis, T. aestivus*, and *T. velantianus*), generally by distillation from the leafy tops and tender stems of the plant. Two commercial varieties of Thyme oil are recognized, the 'red,' the crude distillate, which is deep orange in color, and the 'white,' which is colourless or pale yellow, which is the 'red' rectified by re-distilling. Thyme oil principally contains the phenols thymol and carvacrol, along with borneol, linalool, and cymene, and rosmarinic and ursolic acids. Where an embodiment describes the use of thyme oil white, other embodiments are specifically contemplated in which the thyme oil white is replaced by thyme oil red, thymol, carvacrol, borneol, linalool, cymene, rosmarinic acid, ursolic acid, or a mixture of any of these with each other or with thyme oil white. Particularly preferable are mixtures of thyme oil white and thyme oil red that contain 10% or less thyme oil red, more preferably 5% or less, and most preferably 1%.

Thymol is a monoterpene phenol derivative of cymene, $C_{10}H_{13}OH$, isomeric with carvacrol, found in thyme oil, and extracted as a white crystalline substance. It is also known as hydroxycymene and 5-methyl-2-(1-methylethyl) phenol. Where an embodiment describes the use of thymol, other embodiments are specifically contemplated in which the thymol is replaced by carvacrol, thyme oil white, thyme oil red, or a mixture of any of these with each other or with thyme oil white.

Geraniol, also called rhodinol and 3,7-dimethyl-2,6-octadien-1-ol, is a monoterpenoid and an alcohol. It is the primary part of oil-of-rose and palmarosa oil. It is used in perfumes and as a flavoring. It is also produced by the scent glands of honey bees to help them mark nectar-bearing flowers and locate the entrances to their hives. Geraniol can be obtained in a highly pure form as Geraniol Fine, FCC (Food Chemicals Codex grade), which is 98% minimum pure geraniol and 99% minimum nerol and geraniol. Geraniol can be also be obtained, for example, as Geraniol 60, Geraniol 85, and Geraniol 95. When Geraniol is obtained as Geraniol 60, Geraniol 85, or Geraniol 95, then about forty percent, fifteen percent, or five percent of the oil can be nerol. Nerol is a monoterpene ($C_{10}H_{18}O$), the cis-isomer of geraniol, which can be extracted from attar of roses, oil of orange blossoms and oil of lavender. Citral (3,7-dimethyl-2,6-octadienal or lemonal) is the generic name for the aldehyde form of nerol and geraniol, and can be obtained from lemon myrtly, *Litsea cubeba*, lemongrass, Lemon *verbena*, lemon balm, lemon, and orange. The E-isomer of citral is known as geranial or citral A. The Z-isomer is known as neral or citral B. Where an embodiment describes the use of any form of geraniol, other embodiments are specifically contemplated in which the geraniol is replaced by another form of geraniol (such as Geraniol Fine FCC or any geraniol/nerol mixture), nerol, geranial, neral, citral, or a mixture of any of these with each other or with any form of geraniol. Similarly, Where an embodiment describes the use of any form of citral, other embodiments are specifically contemplated in which the citral is replaced by a form of geraniol (such as Geraniol Fine FCC or any gernaiol/nerol mixture), nerol, geranial, neral, or a mixture of any of these with each other or with citral.

Vanillin (also known as methyl vanillin, vanillic aldehyde, vanilin, and 4-hydroxy-3-methoxybenzaldehyde) is the primary component of the extract of the vanilla bean. In addition to vanillin, natural vanilla extract also contains p-hydroxybenzaldehyde, vanillic acid, piperonal, and p-hydroxybenzoic acid. Synthetic vanillin is used as a flavoring agent in foods, beverages, and pharmaceuticals. Where an embodiment describes the use of vanillin, other embodiments are specifically contemplated in which the vanillin is replaced by natural vanilla extract, p-hydroxybenzaldehyde, vanillic acid, piperonal, ethyl vanillin, or p-hydroxybenzoic acid, or a mixture of any of these with each other or with vanillin.

Lime oil is derived from *Citrus aurantifolia* (also known as *Citrus medica* var. *acida* and *C. latifolia*) of the Rutaceae family and is also known as Mexican and West Indian lime, as well as sour lime. Its chief constituents are α-pinene, β-pinene, camphene, myrcene, p-cymene, d-limonene, γ-terpinene, terpinolene, 1,8-ceneole, linalool, terpinene-4-ol, α-terpineol, neral, geraniol, neral acetate, geranyl acetate, caryophyllene, trans-α-bergamotene, β-Bisabolen, borneol, and citral. It can be obtained in several forms, including Lime Oil 410 (an artificial Mexican-exressed lime oil available from Millennium Specialty Chemicals). Where an embodiment describes the use of any form of lime oil, other embodiments are specifically contemplated in which the lime oil is replaced by α-pinene, β-pinene, camphene, myrcene, p-cymene, d-limonene, γ-terpinene, terpinolene, 1,8-ceneole, linalool, terpinene-4-ol, α-terpineol, neral, geraniol, neral acetate, geranyl acetate, caryophyllene, trans-α-bergamotene, β-Bisabolen, borneol, or citral, or a mixture of any of these with each other or with any form of lime oil.

Black seed oil is obtained from the seeds of *Nigella sativa*. Its chief constituents are carvone, α-pinene, sabinene, β-pinene, and p-cymene, as well as the fatty acids myristic acid, palmitic acid, palmitoleic acid, stearic acid, oleic acid, linoleic acid, linolenic acid, and arachidic acid. Where an embodiment describes the use of any form of black seed oil, other embodiments are specifically contemplated in which the black seed oil is replaced by d-carvone, l-carvone, a racemic mixture of d-carvone and l-carvone, α-pinene, sabinene, β-pinene, or p-cymene, or a mixture of any of these with each other, with any of myristic acid, palmitic acid, palmitoleic acid, stearic acid, oleic acid, linoleic acid, linolenic acid, or arachidic acid or with any form of black seed oil.

Linalool is a naturally-occurring terpene alcohol chemical found in many flowers and spice plants. It is also known as 3,7-dimethylocta-1,6-dien-3-ol. It has two stereoisomeric forms: (S)-(+)-linalool (known as licareol) and (R)-(−)-linalool (known as coriandrol). Linalool can be obtained as linalool coeur (a racemic mixture, CAS number 78-70-6), or in preferred derivative forms such as tetrahydrolinalool (the saturated form), ethyl linalool, linalyl acetate, and pseudo linalyl acetate (7-octen-2-ol, 2-methyl-6-methylene:acetate). Where an embodiment describes the use of any form of linalool, other embodiments are specifically contemplated in which the linalool is replaced by licareol, coriandrol, tetrahydrolinalool, ethyl linalool, linalyl acetate, pseudo linalyl acetate, or a mixture of any of these with each other or with any form of linalool. Similarly, where an embodiment describes the use of tetrahydrolinalool, other embodiments are specifically contemplated in which the tetrahydrolinalool is replaced by licareol, coriandrol, racemic linalool, ethyl linalool, linalyl acetate, pseudo linalyl acetate, or a mixture of any of these with each other or with tetrahydrolinalool. Additionally, where an embodiment describes the use of ethyl linalool, other embodiments are specifically contemplated in which the ethyl linalool is replaced by licareol, coriandrol, tetrahydrolinalool, racemic linalool, linalyl acetate, pseudo linalyl acetate, or a mixture of any of these with each other or with ethyl linalool. Finally, where an embodiment describes the use of linalyl acetate, other embodiments are specifically contemplated in which the linalyl acetate is replaced by licareol, coriandrol, tetrahydrolinalool, racemic linalool, ethyl linalool, pseudo linalyl acetate, or a mixture of any of these with each other or with linalyl acetate.

Isopropyl myristate is the ester of isopropanol and myristic acid; it is also known as 1-tetradecanoic acid, methylethyl ester, myristic acid isopropyl ester, and propan-2-yl tetradecanoate. Where an embodiment describes the use of isopropyl myristate, other embodiments are specifically contemplated in which isopropyl myristate may be replaced by similar chemicals such as isopropyl palmitate, isopropyl isothermal, putty stearate, isostearyl neopentonate, myristyl myristate, decyl oleate, octyl sterate, octyl palmitate, isocetyl stearate, or PPG myristyl propionate, or a mixture of any of these with each other or with isopropyl myristate. Isopropyl myristate may also be used as a thickening agent and emollient.

Piperonal (heliotropine, protocatechuic aldehyde methylene ether) is an aromatic aldehyde that comes as transparent crystals, $C_8H_6O_3$, and has a floral odor. It is used as flavoring and in perfume. It can be obtained by oxidation of piperonyl alcohol. Where an embodiment describes the use of piperonal, other embodiments are specifically contemplated in which piperonal may be replaced by piperonyl alcohol, 3,4-methylenedioxybenzylamine, 3,4-methylenedioxymandelonitrile, piperonylic acid, piperonyl acetate, piperonylacetone, piperonylideneacetone, piperonyl isobutyrate, piperonyl butoxide, piperonylglycine, or protocatecheuic acid or a mixture of any of these with each other or with piperonal. Similarly, where an embodiment describes the use of piperonyl alcohol, other embodiments are specifically contemplated in which piperonyl alcohol may be replaced by piperonal, 3,4-methylenedioxybenzylamine, 3,4-methylenedioxymandelonitrile, piperonylic acid, piperonyl acetate, piperonylacetone, piperonylideneacetone, piperonyl isobutyrate, piperonyl butoxide, piperonylglycine, or protocatecheuic acid, or a mixture of any of these with each other or with piperonyl alcohol.

Triethyl citrate (also known as citric acid, triethyl ester; TEC; ethyl citrate; 2-hydroxy-1,2,3-propanetricarboxylic acid, triethyl ester; and Citroflex 2) is used as a high boiling solvent and plasticizer for vinyl resins and cellulose acetates. It is a plasticizer permitted in the field of food additives, food contact materials, medicines, and pharmaceuticals. Where an embodiment describes the use of triethyl citrate, other embodiments are specifically contemplated in which triethyl citrate may be replaced by other citrate plasticiser esters such as tributyl citrate, acetyl tributyl citrate and tri-(2-ethylhexyl)-citrate, or a mixture of any of these with each other or with triethyl citrate.

Terpines are a class of organic compounds derived from hydrocarbon isoprene ($C_5H_8$) units. Terpines are constituents of essential oils of many plants and flowers. There are many types of terpenes, which are classified by the number of isoprene units in the molecule; examples include monoterpenes and sesquiterpenes. The terpinenes are isomeric hydrocarbons classified as terpenes. Some members of this group are used in a wide variety of flavor and fragrance compositions, as well as in extensions of *citrus* oils. Gamma-terpinene is also known as 1-isopropyl-4-methyl-1,4-cyclohexadiene, 4-methyl-1-(1-methylethyl)-1,4-cyclohexadiene, and p-mentha-1,4-diene. Alpha-terpinene is also known as 4-methyl-1-(1-methylethyl)-1,3-cyclohexadiene. Both alpha- and gamma-terpinene have a lemony fragrance. Beta-terpinene, also known as 4-methylene-1-(1-methylethyl)cyclohexene, has been prepared from sabinene. A derivative, terpinene-4-ol, is the primary active ingredient of tea tree oil and the compound of highest concentration in essential oil of nutmeg. Other monoterpene alcohol derivatives of the erpinenes include the α-, 13-, and γ-terpineol isomers; the α-terpineol isomer is the major component of the naturally isolated terpineol. Other related compounds are terpinolene (4-Isopropylidene-1-methylcyclohexene; p-Menth-1,4(8)-diene; 1-Methyl-4-(1-methylethylidene)cyclohexene; 1-Methyl-4-propan-2-ylidene-cyclohexene), and the isomers α-phellandrene and β-phellandrene. Where an embodiment describes the use of gamma-terpinene, other embodiments are specifically contemplated in which gamma-terpinene may be replaced by other terpinenes or derivatives thereof such as terpinolene, α-phellandrene, β-phellandrene, alpha-terpinene, beta-terpinene, α-terpineol, β-terpineol, γ-terpineol, or terpinene-4-ol, or a mixture of any of these with each other or with gamma-terpinene. Where an embodiment describes the use of alpha-terpinene, other embodiments are specifically contemplated in which alpha-terpinene may be replaced by other terpinenes or derivatives thereof such as terpinolene, α-phellandrene, β-phellandrene, gamma-terpinene, beta-terpinene, α-terpineol, β-terpineol, γ-terpineol, or terpinene-4-ol, or a mixture of any of these with each other or with alpha-terpinene. Where an embodiment describes the use of terpinene-4-ol, other embodiments are specifically contemplated in which terpinene-4-ol may be replaced by other terpinenes or derivatives thereof such as terpinolene, α-phellandrene, β-phellandrene, alpha-terpinene, beta-terpinene, α-terpineol, β-terpineol, γ-terpineol, or gamma-terpinene, or a mixture of any of these with each other or with terpinene-4-ol. Where an embodiment describes the use of α-terpineol, other embodiments are specifically contemplated in which α-terpineol may be replaced by other terpinenes or derivatives thereof such as terpinolene, α-phellandrene, β-phellandrene, alpha-terpinene, beta-terpinene, terpinene-4-ol, β-terpineol, γ-terpineol, or gamma-terpinene, or a mixture of any of these with each other or with α-terpineol. Where an embodiment describes the use of terpinolene, other embodiments are specifically contemplated in which terpinolene may be replaced by other terpinenes or derivatives thereof such as α-terpineol, α-phellandrene, β-phellandrene, alpha-terpinene, beta-terpinene, terpinene-4-ol, β-terpineol, γ-terpineol, or gamma-terpinene, or a mixture of any of these with each other or with terpinolene.

In addition, the use of several long-chain aldehydes, such as octanal, nonanal, decanal, and dodecanal. Where an embodiment describes the use of one such aldehyde, other embodiments are specifically contemplated in which the designated aldehyde is replaced with any of the other aldeydes, or a mixture of any of these aldehydes with each other or with the designated aldehyde.

Tocopherols are a class of chemicals consisting of various methylated phenols, some of which have vitamin E activity. These include α-tocopherol, β-tocopherol, γ-tocopherol, and δ-tocopherol. Also belonging to this family are the tocotrienols, including α-tocotrienol, β-tocotrienol, γ-tocotrienol, and δ-tocotrienol. In preferred embodiments, mixtures of these compositions, such as tocopherol gamma tenox or Tenox GT, are employed. Where an embodiment describes the use of one tocopherol, other embodiments are specifically contemplated in which the designated tocopherol is replaced with any of the other tocopherols, or a mixture of any of these tocopherols with each other or with the designated tocopherol.

Fatty acids, suitable for use herein, can be obtained from natural sources such as, for instance, plant or animal esters (e.g. palm oil, rape seed oil, palm kernel oil, coconut oil, babassu oil, soybean oil, castor oil, tallow, whale or fish oils, grease, lard, and mixtures thereof). Fatty acids derived from plant sources are preferred. Normally purified or distilled unsaturated and/or saturated fatty acids will be employed, but naturally occurring mixtures may also be used where appropriate, e.g. when high in unsaturated fatty acids such as soybean, linseed, sunflower, corn, onagra, and/or borage, oil fatty acids. The fatty acids may also be synthetically prepared, for example as described in "Fatty Acids in Industry", Ed Robert W Johnson, Earl Fritz, Marcel Dekker Inc, 1989 ISBN 0-8247-7672-0.

The unsaturated and saturated fatty acids used in the methods of the present invention are in the form of the free fatty acid and/or salt thereof. Suitable salts are alkali metal salts, such as sodium, and/or potassium; ammonium salts; and/or alkylamine salts, such as isopropylamine, aminomethylpropanol, monoethanolamine, diethanolamine, and/or triethanolamine. Alkali metal, particularly potassium, salts are preferred.

The fatty acid salts are preferably formed in situ by the addition of suitable salt forming material, e.g. base, such as sodium hydroxide, preferably potassium hydroxide, to the fatty acid containing composition. The base is preferably added as a relatively dilute aqueous solution, e.g. at a concentration of 1 to 30%, preferably 5 to 20%, more preferably about 10 to 15% w/w. The addition of base can be used to control the pH of the composition which is preferably in the range from 6 to 9, more preferably 7 to 8.5, particularly 7.2 to 8.2, and especially 7.5 to 8. A surprising improvement in the pest control properties of the composition can be achieved at these pH values.

In one embodiment, the amount of fatty acid salts in the composition is preferably in the range from 50 to 100%, more preferably 90 to 99.9%, particularly 95 to 99.5%, and especially 96 to 99% by weight, based on the total amount of fatty acids and salts thereof in the composition. Correspondingly, the amount of free fatty acids is preferably in the range from 0 to 50%, more preferably 0.1 to 10%, particularly 0.5 to 5%, and especially 1 to 4% by weight, based on the total weight of fatty acids and salts thereof in the composition.

The fatty acids and/or salts thereof are suitably present in a composition according to various methods of the present invention in the range from 3 to 50%, preferably 5 to 40%, more preferably 10 to 30%, particularly 15 to 25%, and especially 18 to 22% by weight, based on the total amount of the composition.

The unsaturated fatty acids and/or salts thereof used in the methods of the present invention comprise, consist essentially of, or consist of, in the range from 12 to 26, preferably 14 to 24, more preferably 16 to 22, particularly 18 to 20, and especially 18 carbon atoms. In one embodiment, greater than 50%, preferably greater than 60%, more preferably greater than 70%, particularly greater than 80%, and especially greater than 90% and up to 100% by weight of the unsaturated fatty acids fall within one or more of the above carbon atom ranges, based on the total weight of unsaturated fatty acids in the composition.

Suitable unsaturated fatty acids are selected from the group consisting of oleic, elaidic, ricinoleic, dodecenoic, tetradecenoic (myristoleic), hexadecenoic (palmitoleic), octadecadienoic (linoleic or linolelaidic), octadecatrienoic (linolenic), eicosenoic (gadoleic), eicosatetraenoic (arachidonic), docosenoic (erucic), docosenoic (brassidic), docosapentaenoic (clupanodonic), eicosapentaenoic, docosahexaenoic, gamma-linolenic, dihomo-gamma-linolenic, arachidonic, acids, and mixtures thereof. Preferred unsaturated fatty acids are selected from the group consisting of oleic, ricinoleic, linoleic, linolenic, acids and mixtures thereof. Particularly preferred unsaturated fatty acids are selected from the group consisting of oleic, ricinoleic, linoleic, acids and mixtures thereof.

The unsaturated fatty acids are preferably monocarboxylic acids and may be linear or branched, and are preferably linear. The unsaturated fatty acids may be in the form of cis and/or trans isomers. Oleic acid is a preferred cis isomer, and elaidic acid a preferred trans isomer. The unsaturated fatty acids may be unsubstituted, or substituted, for example with one or more hydroxyl groups. Ricinoleic acid is a preferred hydroxy acid.

The unsaturated fatty acids may be mono-unsaturated, di-unsaturated or polyunsaturated, i.e. containing one, two or more than two carbon-carbon double bonds respectively. Oleic acid is a preferred mono-unsaturated fatty acid, and linoleic acid is a preferred di-unsaturated fatty acid. In one embodiment, the concentration of (i) mono-unsaturated fatty acids is preferably greater than 10%, more preferably greater than 20%, and particularly in the range from 30 to 90%, by weight, (ii) di-unsaturated fatty acids is preferably greater than 5%, more preferably greater than 10%, and particularly in the range from 15 to 50% by weight, (iii) mono-unsaturated and di-unsaturated fatty acids combined is preferably greater than 75%, more preferably greater than 85%, particularly greater than 90%, and especially in the range from 95 to 100% by weight, and/or (iv) polyunsaturated fatty acids is preferably less than 25%, more preferably less than 15%, particularly less than 5%, and especially in the range from 0 to 3% by weight, all based on the total weight of unsaturated fatty acids in the composition.

The concentration of unsaturated fatty acids and/or salts thereof present in a composition useful in the methods of the present invention is suitably in the range from 10 to 90%, preferably 20 to 80%, more preferably 30 to 70%, particularly 40 to 60%, and especially 45 to 55% by weight, based on the total weight of fatty acids and/or salts thereof in the composition.

In certain compositions useful in an embodiment of the present invention, the unsaturated fatty acids used in various methods of the invention comprise a mixture of unsubstituted fatty acids and hydroxy fatty acids, preferably present at a ratio of 10 to 90%:10 to 90%, more preferably 30 to 70%:30 to 70%, particularly 40 to 60%:40 to 60%, and especially 45 to 55%:45 to 55% by weight, based on the total weight of unsaturated fatty acids in the composition. A particularly preferred combination is a mixture of oleic acid and ricinoleic acid.

The saturated fatty acids and/or salts thereof used in various methods of the present invention comprise, consist essentially of, or consist of, in the range from 6 to 14, preferably 6 to 12, more preferably 8 to 12, and particularly 8 to 10 carbon atoms. In one embodiment, greater than 50%, preferably greater than 60%, more preferably greater than 70%, particularly greater than 80%, and especially greater than 90% and up to 100% by weight of the saturated fatty acids fall within one or more of the above carbon atom ranges, based on the total weight of saturated fatty acids in the composition.

The saturated fatty acids are preferably monocarboxylic acids and may be linear and/or branched, and are preferably linear.

Suitable saturated fatty acids are selected from the group consisting of hexanoic (caproic), octanoic (caprylic), nonanoic, decanoic (capric), undecanoic, dodecanoic (lauric), tridecanoic, tetradecanoic acid (myristic), 2-ethyl hexanoic, trimethylhexanoic, trimethylnonanoic, acids and mixtures thereof. Preferred saturated fatty acids are selected from the group consisting of caprylic, capric, 2-ethyl hexanoic, trimethylhexanoic, trimethylnonanoic, tetramethylhexanoic, acids, and mixtures thereof. Particularly preferred saturated fatty acids are selected from the group consisting of caprylic, capric, 2-ethyl hexanoic, trimethylhexanoic, acids, and mixtures thereof.

Lauric acid is a saturated fatty acid with a 12-carbon atom chain, and is found naturally in coconuts. Lauric acid is also known as dodecanoic acid. The combination of lauric acid and at least one oil appears to provide increased efficacy in terms of repellency against various arthropods.

The concentration of saturated fatty acids and/or salts thereof present in a composition according to methods of the present invention is suitably in the range from 10 to 90%, preferably 20 to 80%, more preferably 30 to 70%, particularly 40 to 60%, and especially 45 to 55% by weight, based on the total weight of fatty acids and/or salts thereof in the composition.

The ratio by weight of unsaturated fatty acids and/or salts thereof to saturated fatty acids and/or salts thereof in a composition according to various methods of the present invention is preferably in the range from 0.2 to 5:1, more preferably 0.35 to 3:1, particularly 0.5 to 2:1, and especially 0.8 to 1.2:1.

In one embodiment, the mean number of carbon atoms, on a weight basis, present in the unsaturated fatty acids and/or salts is suitably at least 2, preferably at least 4, more preferably in the range from 6 to 12, particularly 7 to 11, and especially 8 to 10 carbon atoms greater than the mean number of carbon atoms present in the saturated fatty acids and/or salts. The mean number of carbon atoms by weight present in the unsaturated fatty acids and/or salts is preferably in the range from 14 to 22, more preferably 16 to 20, particularly 17 to 19, and especially 17.5 to 18.5. The mean number of carbon atoms by weight present in the saturated fatty acids and/or salts is preferably in the range from 6 to 12, more preferably 7 to 11, particularly 8 to 10, and especially 8.5 to 9.5.

In those compositions including more than one oil, each oil can make up between about 0.1%, or less, to about 99%, or more, by weight, of the composition mixture. For example, one composition of the present invention comprises about 1% thymol and about 99% geraniol. Optionally, the compositions can additionally comprise a fixed oil, which is a non-volatile non-scented plant oil. Fixed oils may stabilize the composition, limiting the evaporation of the active components. Fixed oils useful in the formulations of the present invention include, but are not limited to, castor oil, corn oil, cottonseed oil, cumin oil, linseed oil, mineral oil, white mineral oil, olive oil, peanut oil, safflower oil, sesame oil, and soybean oil.

In certain exemplary embodiments, arthropod control compositions according to the invention include at least one of geraniol, lauric acid, vanillin, isopropyl myristate, triethyl citrate, and vitamin e. In certain exemplary embodiments, arthropod control compositions according to the invention include at least two of geraniol, lauric acid, vanillin, isopropyl myristate, triethyl citrate, and vitamin e. In certain exemplary embodiments, arthropod control compositions according to the invention include geraniol, lauric acid, vanillin, isopropyl myristate, triethyl citrate, and vitamin e. In certain exemplary embodiments, arthropod control compositions according to the invention include geraniol, lauric acid, vanillin, isopropyl myristate, and triethyl citrate. In certain exemplary embodiments, arthropod control compositions according to the invention include geraniol, lauric acid, vanillin, and triethyl citrate. In certain exemplary embodiments, arthropod control compositions according to the invention include geraniol, lauric acid, vanillin, and isopropyl myristate. In certain exemplary embodiments, arthropod control compositions according to the invention include geraniol, lauric acid, and vanillin. In certain exemplary embodiments, arthropod control compositions according to the invention include geraniol and lauric acid.

While embodiments of the invention can include active ingredients, carriers, inert ingredients, and other formulation components, preferred embodiments begin with a primary blend. A primary blend is preferably a synergistic combination containing two or more active ingredients and, optionally, additional ingredients. The primary blends can then be combined with other ingredients to produce a formulation. Accordingly, where concentrations, concentration ranges, or amounts, are given herein, such quantities typically are in reference to a primary blend or blends. Thus, when a primary blend is further modified by addition of other ingredients to produce a formulation, the concentrations of the active ingredients are reduced proportional to the presence of other ingredients in the formulation.

In preferred blends, geraniol can be included at a concentration of between 5% or less to 50% or more; at a concentration between 10%-40%; at a concentration of about 13%; at a concentration of about 19%; at a concentration of about 28%; or at a concentration of about 33% by weight.

In preferred blends, lauric acid can be included at a concentration of between 10% or less to 70% or more; at a concentration between 25%-70%; at a concentration of about 27%; at a concentration of about 37%; at a concentration of about 57%; or at a concentration of about 67% by weight.

In preferred blends, vanillin can be included at a concentration of between 2.5% or less to 20% or more; at a concentration between 5%-15%; at a concentration of about 7%; at a concentration of about 9%; or at a concentration of about 14% by weight.

In preferred blends, isopropyl myristate can be included at a concentration of between 10% or less to 50% or more; at a concentration between 25%-50%; at a concentration of about 25%; at a concentration of about 28%; at a concentration of about 35%; or at a concentration of about 41% by weight.

In preferred blends, triethyl citrate can be included at a concentration of between 9% or less to 40% or more; at a concentration between 20%-40%; at a concentration of about 25%; at a concentration of about 34%; or at a concentration of about 37% by weight.

In preferred blends, vitamin E can be included at a concentration of between 0.1% or less to 5% or more; at a concentration between 0.1%-0.8%; or at a concentration of about 0.3% by weight.

Any blends of the invention can be diluted to varying degrees. The ratios of ingredients expressed by the amounts listed are also embodiments of the invention.

The compositions of the present invention can comprise, in admixture with one or more suitable carrier and optionally with a suitable surface active agent and/or one or more surfactant agents, plant essential oil compounds and/or derivatives thereof, natural and/or synthetic, including racemic mixtures, enantiomers, diastereomers, hydrates, salts, solvates and metabolites, etc.

In some embodiments, the composition can be comprised of geraniol, lauric acid and mineral oil. In some embodiments, the concentration of geraniol present in the composition can be 4.1-6%, 3.1-7%, 2.1-8%, 1.1-9%, or 0.1-10%. In some embodiments, the concentration of lauric acid present in the composition can be 8.5-12%, 7-14%, 5.5-16%, 4-18%, or 2.5-20%. In some embodiments, the concentration of mineral oil in the composition can be 33.2-43.2%, 24.9-44.9%, 16.6-46.6%, 8.3-48.3%, or 0-50%. In some embodiments the composition comprises 5% geraniol, 10% lauric acid, and 41.5% mineral oil. In some embodiments, the concentration ratio of geraniol:lauric acid:mineral oil is 1:2:8.3.

In some embodiments, the composition can be comprised of 7.4-11.6%, 5.6-14%, 3.7-16.3%, 1.9-18.7%, or 0-21% triethyl citrate.

In some embodiments, the composition can be comprised of 2-2.6%, 1.5-2.7%, 1-2.8%, 0.5-2.9%, 0-3% vanillin In some embodiments, the composition can be comprised of 9-13.5%, 7.4-16.4%, 5.7-19.2%, 4.1-22.1%, or 2.5-25% isopropyl myristate.

In some embodiments, the composition can be comprised of 19.9-33.9, 18.7-46.7%, 17.4-59.4%, 16.2-72.2%, 15-85% isopropyl alcohol.

In some embodiments, the composition can be comprised of 0.1-0.6%, 0.1-1.1%, 0.1-1.5%, 0.1-2%, or 0.1-2.5% vitamin E.

A suitable carrier can include any carrier in the art known for plant essential oils, provided the carrier does not adversely affect the compositions of the present invention. The term "carrier" as used herein means an inert or fluid material, which can be inorganic or organic and of synthetic or natural origin, with which the active compound is mixed or formulated to facilitate its application to the host, area, or other object to be treated, or to facilitate its storage, transport and/or handling. In general, any of the materials customarily employed in formulating repellents, pesticides, herbicides, or fungicides, are suitable.

The compositions of the present invention can be employed alone or in the form of mixtures with such solid and/or liquid dispersible carrier vehicles and/or other known compatible active agents such as other repellents, pesticides, or acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

The compositions of the present invention can be formulated or mixed with, if desired, conventional inert pesticide diluents or extenders of the type usable in conventional arthropod control agents, e.g., conventional dispersible carrier vehicles such as gases, solutions, emulsions, suspensions, emulsifiable concentrates, spray powders, pastes, soluble powders, wettable powders, dusting agents, granules, foams, mousses, pastes, tablets, aerosols, amorphous silica, natural and synthetic materials impregnated with active compounds, microcapsules, coating compositions for use on seeds, and formulations used with burning equipment, such as fumigating cartridges, fumigating cans and fumigating coils, as well as ULV cold mist and warm mist formulations, etc.

The compositions of the present invention can further comprise surface-active agents. Examples of surface-active agents that can be employed with the present invention, include emulsifying agents, such as non-ionic and/or anionic emulsifying agents (e.g., polyethylene oxide esters of fatty acids, polyethylene oxide ethers of fatty alcohols, cyclodextrins, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents such as lignin, sulfite waste liquors, methyl cellulose, etc.

In some embodiments, water-based formulations are preferred. Although oil-based formulations of arthropod control agents are generally more effective, water-based formulations have the advantage that they do not leave behind an oily residue on treated surfaces.

The surfactant of the water-based formulation is provided to facilitate mixture of the arthropod control composition with the water. The surfactant may include an end having a carboxyl group, which will face the water molecules, and a hydrocarbon end, which will face an oil component of the arthropod control composition. As such, the surfactant allows the water and the oil component of the composition to be mixed to form an emulsion. Various surfactants may be used in the formulation of the present invention, for example, sodium lauryl sulfate (SLS, anionic), chlorhexidine (CLH, cationic), and Poloxamer 407 (POL407, non-ionic), Sodium dodecylsulfate (SDS), Sodium cholate, Sodium deoxycholate, N-Lauroylsarcosine, Lauryldimethylamine-oxide (LDAO), Cetyltrimethylammoniumbromide (CTAB), Bis(2-ethylhexyl)sulfosuccinate, potassium salts of fatty acids, or mixtures thereof.

The solvent of the water-based formulation serves to reduce the water-oil surface tension of the emulsion or composition. By reducing this surface tension, the oil spots are more readily dispersed in the water, and a thin film of the oil-water mixture is allowed to form on the treated surfaces, which surfaces may include a host, areas within a household, outdoor areas, plants and the arthropods themselves. The solvent may also serve as a carrier and a synergist. The solvent may assist in fast penetration through the cell membrane of an arthropod being controlled to ensure the arrival of sufficient active ingredients to the site of action. The solvent may assist in wetting the arthropod exoskeleton to facilitate exposure of the cell membrane to the formulation and/or may dissolve portions of the exoskeleton. The solvent is suitably relatively polar, and preferably is a lower alcohol or ester having a molecular weight of less than 400, more preferably less than 200, and particularly in the range from 40 to 100. Isopropanol and/or ethanol are particularly preferred lower alcohol cosolvents. Various solvents may be used, for example, mineral oil, white mineral oil, isopar M, isopar C, alcohol, ethanol, isopropanol, or mixtures thereof.

To produce the water-based formulation, the arthropod control composition containing one or more plant essential oils is mixed with water to create a slurry. The surfactant is then added to create certain embodiments of the water-based formulation. To create other embodiments of the water-based formulation, the solvent is then added. The final concentration of the arthropod control composition in the formulation may be, for example, about 10-25%. The final concentration of the surfactant in the formulation may be, for example, about 1-10%. The final concentration of the solvent in the formulation may be, for example, 0 to about 80%. Some embodiments of the present invention are characterized by rapid killing, e.g., kill-on-contact, and some embodiments are characterized by residual effects, i.e., formulation remains on treated surface affecting arthropod control for an extended period of time. In the case of the embodiment characterized by residual effects, it should be noted that the solvent-component of the formulation is not necessary. In such embodiments of the invention, the formulation includes: water, an arthropod control composition, a surfactant, and a stabilizer. Such embodiments may optionally include the solvent described herein.

Once the water-based formulation has been prepared, it may be applied to a desired host, area, or object to affect arthropod control. Once applied, it will form a thin film on the treated surfaces, adhering thereto and providing effective arthropod control. The formulation may be applied to the host, area, or object in a variety of manners known in the art, for example, the formulation may be prepared as an aerosol or trigger spray.

Certain mixtures of liquefied hydrocarbons, such as propellants A-46, A-70, or 142A may be used as propellants in embodiments of spray mixtures. Where an embodiment describes the use of one propellant, other embodiments are specifically contemplated in which the designated propellant is replaced with any of the other propellant, or a mixture of any of these propellants with each other or with the designated propellant.

In certain exemplary embodiments, the present invention encompasses a mixture of an arthropod control composition including one or more plant essential oils with a carrier. For example, embodiments of the present invention can include a carrier having a surface area, with the arthropod control composition coated on the surface area of the carrier. The carrier may be, for example, crystals, powder, dust, granules or the like, which provides an absorption surface area for the arthropod control compositions. One example of a carrier that can be used in accordance with the present invention is diatomaceous earth (DE). DE is a naturally occurring sedimentary rock that is easily crumbled into a fine powder. This powder has an abrasive feel, similar to pumice powder, and is very light, due to its high porosity. Diatomaceous earth consists of fossilized remains of diatoms, a type of hard-shelled algae.

To produce certain embodiments of the present invention, the carrier and the arthropod control composition are mixed to allow the carrier to become coated with the composition.

In some embodiments of the invention, after the carrier has been coated with the arthropod control composition to form the formulation, the formulation can be applied to a desired host, area, or object to affect arthropod control. Because the carrier reduces the volatility of the arthropod control composition, the composition will remain active for an amount of time that is greater than the time the composition, alone, i.e., unformulated composition, would remain active. As such, the formulation continues to provide arthropod control after the time by which the composition, alone, would have volatilized.

Embodiments of the present invention can be used to control arthropods by treating an area directly. For example, the area can be treated by spreading or dispersing the formulation, for example, manually, automatically, with a fertilizer spreader, or the like.

An area can be treated with a composition of the present invention, for example, by using a spray formulation, such as an aerosol or a pump spray, or a burning formulation, such as a candle or a piece of incense containing the composition. Of course, various treatment methods can be used without departing from the spirit and scope of the present invention. For example, compositions can be comprised in household products such as: air fresheners (including heated air fresheners in which arthropod repellent substances are released upon heating, e.g., electrically, or by burning); hard surface cleaners; or laundry products (e.g., laundry detergent-containing compositions, conditioners).

In certain embodiments of the invention, an area can be treated with a composition of the present invention, for example, by using a spray formulation, such as an aerosol or a pump spray, or a burning formulation, such as a candle or a piece of incense containing the composition, or the like. In certain embodiments of the invention, an area can be treated, for example, via aerial delivery, by truck-mounted equipment, or the like. Of course, various treatment methods can be used without departing from the spirit and scope of the present invention. For example, compositions can be comprised in household products, for example, hard surface cleaners, and the like.

An exemplary dispenser of a system of the present invention can deliver a pest control composition to the atmosphere in a continuous manner over a period of time. The exemplary dispenser can include a reservoir for holding a pest control composition, and a wick for drawing the composition from the reservoir and releasing the arthropod control composition into the atmosphere. The reservoir can be constructed from a material that is impermeable to the pest control composition, for example, appropriate glass, ceramic, or polymeric materials can be used. The reservoir can include an aperture, which can be sealed or unsealed, as desired. When the exemplary system of the present invention is not in use, the aperture can be sealed to prevent the release of the pest control composition into the atmosphere. It may be desirable, for example, to seal the aperture when the exemplary system is being stored or transported. When the system is in use, the aperture is unsealed, such that the wick can draw the pest control composition from the reservoir, and release the control composition through the aperture into the atmosphere.

In certain embodiments of the invention, the rate of release of the composition can be controlled, for example, by making adjustments to the wick of the dispenser. For example, the surface area of the wick that is exposed to the atmosphere can be altered. Generally, the greater the exposed surface area, the greater the rate of release of the pest control composition. In this regard, in certain embodiments, the dispenser can include multiple wicks and the reservoir can include multiple apertures through which the arthropod control composition can be released into the atmosphere. As another example, the wick can be constructed from a particular material that draws the pest control composition from the reservoir and releases it into the environment at a desired rate, such as, for example, a wick made of wood, a wick made of a synthetic fiber, or the like.

Another exemplary dispenser of a system of the present invention can deliver an arthropod control composition to a desired area. The dispenser can include a sealed pouch that can be constructed from a material that is impermeable to the arthropod control composition, for example, a metallic foil, a polymeric material, or the like. The pouch can define a volume for holding the arthropod control composition. The composition can be provided in a material disposed within the volume of the pouch, for example, a sponge, a cloth saturated with the material, or the like. When it becomes desirable to place the exemplary system into use, the pouch can be unsealed, exposing the composition for release into the atmosphere or for application to a desired area.

In certain embodiments the arthropod control composition is provided in a saturated cloth within the pouch, which can be used to apply the control composition a desired area. For example, a desired area can be an animal, such as a human, a domestic animal, surfaces within a dwelling, an outdoor living area, or the like.

In certain embodiments the arthropod control composition is provided in a concentrate that may be, for example, tank mixed. In certain embodiments the arthropod control composition is provided in a pouch that can be mixed with water and other adjuvents.

In certain embodiments, the dispenser can further include a hook, allowing the pouch and exposed control composition to be hung in a desired location, such as in a closet or a pantry.

In certain embodiments, a method of the present invention can deliver an arthropod control composition to a desired area. In certain embodiments, a dispenser used with the method can be constructed from a substantially planar, integral piece of material, having a first side that is coated with control composition, and a second side that is not coated with control composition. The integral piece of material can be folded and sealed such that the side coated with the control composition is contained within the volume defined by the sealed pouch. When the pouch is unsealed, the side that is coated with control composition is exposed. The substantially planar piece of material can be placed in a desired location to deliver control composition to the atmosphere, or to crawling arthropods that walk across the material.

Another exemplary dispenser of a system of the present invention can deliver an arthropod control composition to a desired area. The control composition can be incorporated into an appropriate material. In certain embodiments, the composition-containing material can be a material that is capable of controlling the release rate of the control composition, i.e., controlled-release material, allowing the control composition to be released into the atmosphere at a desired rate that can be adjusted by providing controlled-release material having appropriate specifications. The controlled-release material can be constructed from an appropriate polymer. In other embodiments the composition-containing material does not allow the control composition to be released into the atmosphere, but rather retains the control composition. An optional casing that is impermeable to the arthropod control composition can be provided to hold the composition-containing material until the system is ready for use. When the system is ready for use, the casing can be peeled away, exposing the composition-containing material. The composition-containing material can be placed in a desired location to deliver control composition to crawling arthropods that walk across the material, or to deliver the control composition to the atmosphere when a controlled-release material is used, e.g., control flying arthropods.

In certain embodiments, the composition-containing material can have a substantially planar design, appropriate for positioning adjacent a mattress for controlling bed bugs, e.g., *Cimex lectularius*. A substantially planar design can also be used, for example, as or with a picnic table cloth. In certain embodiments, the composition-containing material can be used as ground cover for a garden bed or adjacent crop plants to control weeds. In certain embodiments, the composition-containing material can take the shape of a bag, and could be used for trash collection, while controlling arthropods commonly attracted to household garbage or other trash.

Another exemplary dispenser of a system of the present invention can be a substantially dry sheet containing the control composition, which control composition can be applied to a desired location upon exposing the cloth to water or an aqueous liquid, e.g., perspiration. In certain embodiments, the dry sheet containing the control composition can dissolve into a cream or gel when exposed to water or an aqueous liquid, which can then be applied to a desired area. For example, a desired area can be an animal, such as a human, a domestic animal, or another animal.

The compositions of the present invention can be used to control arthropods by either treating a host directly, or treating an area in which the host will be located. For example, the host can be treated directly by using a cream or spray formulation, which can be applied externally or topically, e.g., to the skin of a human. A composition can be applied to the host, for example, in the case of a human, using formulations of a variety of personal products or cosmetics for use on the skin or hair. For example, any of the following can be used: fragrances, colorants, pigments, dyes, colognes, skin creams, skin lotions, deodorants, talcs, bath oils, soaps, shampoos, hair conditioners and styling agents.

The present invention comprises compositions for controlling arthropods and methods for using these compositions. The present invention comprises compositions for controlling arthropods, which comprise one or more plant essential oils and methods for using these compositions. In those compositions including more than one oil, each oil can make up between about 0.1% to about 99%, by weight, of the composition mixture. For example, one composition of the present invention comprises about 1% thymol and about 99% geraniol. The plant essential oils, when combined, can have a synergistic effect. The compositions of the present invention can include any of the following oils listed below, or mixtures thereof:

| | | |
|---|---|---|
| trans-anethole | lime oil | piperonyl |
| Black seed oil (BSO) | d-limonene | piperonyl acetate |
| camphene | linalyl anthranilate | piperonyl alcohol |
| catnip oil | linalool | piperonyl amine |
| carvacrol | lindenol | quinone |
| d-carvone | methyl citrate | sabinene |
| l-carvone | methyl di-hydrojasmonate | α-terpinene |
| 1,8-cineole | myrcene | terpinene 900 |
| p-cymene | perillyl alcohol | α-terpineol |
| dodecanoic acid | phenyl acetaldehyde | gamma-terpineol |
| diethyl phthalate | phenylethyl alcohol | 2-tert-butyl-p-quinone |
| eugenol | phenylethyl propionate | α-thujone |
| geraniol | α-pinene | thyme oil |
| isopropyl citrate | β-pinene | thymol |
| lauric acid | piperine | white pepper |
| lemon grass oil | piperonal | wintergreen oil |
| lilac flower oil (LFO) | | Nootkatone |

The compositions of the present invention may also include any of the following oils listed below, or mixtures thereof:

| | | |
|---|---|---|
| Allyl sulfide | α-farnesene | 1-octanol |
| Allyl trisulfide | (Z,E)-α-farnesene | E ocimenone |
| Allyl-disulfide | E-β-farnesene | Z ocimenone |
| Anethole | Fenchone | 3-octanone |
| t-anethole | Forskolin | Ocimene |
| Artemisia alcohol acetate | Furanodiene | Octyl acetate |
| Benzaldehyde | Furanoeudesma-1,3-diene | PD 98059 |
| Benzoic acid | Furanoeudesma-1,4-diene | Peanut oil |
| Benzyl acetate | Furano germacra | Perillyl alcohol |
| Benzyl alcohol | 1,10(15)-diene-6-one | Peppermint oil |
| Bergamotene | Furanosesquiterpene | Permethrin |
| β-bisabolene | Garlic oil | α-phellandrene |
| Bisabolene oxide | Geraniol | β-phellandrene |
| α-bisabolol | Geraniol acetate | Phenethyl propionate |
| Bisabolol oxide | Germacrene D | Phenyl acetaldehyde |

| | | |
|---|---|---|
| Bisobolol oxide β | Germacrene B | Piperonal |
| Bornyl acetate | Grapefruit oil | Piperonyl |
| β-bourbonene | α-gurjunene | Piperonyl acetate |
| Butyl lactate | α-humulene | Piperonyl alcohol |
| Black seed oil | α-ionone | Piperonyl amine |
| α-cadinol | β-ionone | α-pinene |
| Camphene | Isoborneol | β-pinene |
| α-campholene | Isofuranogermacrene | Pine oil |
| α-campholene aldehyde | Iso-menthone | Trans-pinocarveol |
| camphor | Isopropanol | Prenal |
| carvacrol | Isopropyl alcohol | Propargite |
| d-carvone | Isopropyl Myristate | Pulegone |
| l-carvone | Isopropyl citrate | Pyrethrum |
| trans-caryophyllene | Iso-pulegone | Quinine |
| castor oil | Jasmone | Rosemary oil |
| cedar oil | cis-jasmone | Sabinene |
| carbaryl | Lanolin | Sabinyl acetate |
| 1,8-cineole | Lauric acid | Safflower oil |
| Caryophyllene oxide | Lavandustin A | α-santalene |
| Chamazulene | Lecithin | Santalol |
| Chrysanthemate ester | Lemon oil | Sativen |
| Chrysanthemic acid | Lemon grass oil | δ-selinene |
| Chrysanthemyl alcohol | Lilac flower oil | β-sesquphelandrene |
| Cinnamaldehyde | Lime oil | Silicone fluid |
| cinnamyl alcohol | Limonene | Sodium dodecyl sulfate |
| cinnamon oil | d-limonene | Sodium lauryl sulfate |
| Cinnamon bark oil | Linalool | Soybean oil |
| Cinnamon leaf oil | Linalyl acetate | Spathulenol |
| Cis-verbenol | Linalyl anthranilate | Tagetone |
| Citral A | Lindestrene | Tangerine oil |
| Citral B | Lindenol | Tamoxifen |
| Citronellal | Linseed oil | Tebufenozide |
| Citronella oil | Methyl-allyl-trisulfide | α-terpinene |
| Citronellol | Menthol | Terpinene 900 |
| Citronellyl acetate | 2-methoxy furanodiene | α-terpineol |
| Citronellyl formate | menthone | α-terpinolene |
| Clove oil | Menthyl acetate | Gamma-terpineol |
| α-copaene | Methyl acetate | α-terpinyl acetate |
| cornmint oil | Methyl salicylate | tetrahydrofurfuryl alcohol |
| Corn oil | Methyl cinnamate | α-thujone |
| β-costol | Mint | Thyme oil |
| Cryptone | p-cymene | thymol |
| Curzerenone | Mineral oil | Thymyl methyl ether |
| Cumin oil | Musk abrette | Tocopherol |
| d-Carvone | Myrcene | Trans-caryophyllene |
| l-Carvone | Nepetalactone | Trans-pinocarveol |
| Davanone | Menthyl salicylate | Trans-verbenol |
| Diallyl tetrasulfide | Myrtenal | Cis-verbenol |
| diethyl phthalate | Neraldimethyl acetate | Triethyl Citrate |
| Dihydropyrocurzerenone | Nerolidol | Valeric anhydride |
| Dihydrotagentone | Nonanone | Vanillin |
| Vitamin E | Gamma-nonalactone | Verbenone |
| Nootkatone | Oil of pennyroyal | White Mineral Oil |
| Dodecanoic acid | Olive oil | Yomogi alcohol |
| β-elemene | Orange sweet oil | Zingiberene |
| gamma-elemene | Orange oil | Catnip oil |
| Elmol | | Catmint oil |
| Estragole | | |
| 2-ethyl-2-hexen-1-ol | | |
| Eugenol acetate | | |
| Eugenol | | |

Optionally, the compositions can additionally comprise a fixed oil, which is a non-volatile non-scented plant oil. For example, the composition could include one or more of the following fixed oils listed below:

| | | |
|---|---|---|
| castor oil | linseed oil | safflower oil |
| corn oil | mineral oil | sesame oil |
| cottonseed oil | olive oil | soybean oil |
| cumin oil | peanut oil | |

In some embodiments of the compositions, it can be desirable to include compounds each having a purity of about 60%, 65%, 70%, 75%, 80%, 85%, 90%, or 95%. For example, in some embodiments of the compositions that include geraniol, it can be desirable to include a geraniol that is at least about 60%, 85% or 95% pure. In some embodiments, it can be desirable to include a specific type of geraniol. For example, in some embodiments, the compositions can include: geraniol 60, geraniol 85, or geraniol 95. When geraniol is obtained as geraniol 60, geraniol 85, or geraniol 95, then forty percent, fifteen percent, or five percent of the oil can be Nerol. Nerol is a monoterpene (C10H18O) that can be extracted from attar of roses, oil of orange blossoms and oil of lavender. Embodiments of the present invention can include art-recognized ingredients normally used in such formulations. These ingredients can include, for example, antifoaming agents, anti-microbial agents, anti-oxidants, anti-redeposition agents, bleaches, colorants, emulsifiers, enzymes, fats, fluorescent materials, fungicides, hydrotropes, moisturizers, optical brighteners, perfume carriers, perfume, preservatives, proteins, silicones, soil release agents, solubilizers, sugar derivatives, sun screens, surfactants, vitamins, waxes, and the like.

In certain embodiments, embodiments of the present invention can also contain other adjuvants or modifiers such as one or more therapeutically or cosmetically active ingredients. Exemplary therapeutic or cosmetically active ingredients useful in the compositions of the invention can include, for example, fungicides, sunscreening agents, sun-blocking agents, vitamins, tanning agents, plant extracts, anti-inflammatory agents, anti-oxidants, radical scavenging agents, retinoids, alpha-hydroxy acids, emollients (such as adipic acid), antiseptics, antibiotics, antibacterial agents, antihistamines, and the like, and can be present in an amount effective for achieving the therapeutic or cosmetic result desired.

In some embodiments, compositions of this invention can include one or more materials that can function as an antioxidant, such as reducing agents and free radical scavengers. Suitable materials that can function as an antioxidant can include, for example: acetyl cysteine, ascorbic acid, t-butyl hydroquinone, cysteine, diamylhydroquinone, erythorbic acid, ferulic acid, hydroquinone, p-hydroxyanisole, hydroxylamine sulfate, magnesium ascorbate, magnesium ascorbyl phosphate, octocrylene, phloroglucinol, potassium ascorbyl tocopheryl phosphate, potassium sulfite, rutin, sodium ascorbate, sodium sulfite, sodium thloglycolate, thiodiglycol, thiodiglycolamide, thioglycolic acid, thiosalicylic acid, tocopherol, tocopheryl acetate, tocopheryl linoleate, tris(nonylpheny)phosphite, and the like.

Embodiments of the invention can also include one or more materials that can function as a chelating agent to complex with metallic ions. This action can help to inactivate the metallic ions for the purpose of preventing their adverse effects on the stability or appearance of a formulated composition. Chelating agents suitable for use in an embodiment of this invention can include, for example, aminotrimethylene phosphonic acid, beta-alanine diacetic acid, calcium disodium EDTA, citric acid, cyclodextrin, cyclohexanediamine tetraacetic acid, diammonium citrate, diammonium EDTA, dipotassium EDTA, disodium azacycloheptane diphosphonate, disodium EDTA, disodium pyrophosphate, EDTA (ethylene diamine tetra acetic acid), gluconic acid, HEDTA (hydroxyethyl ethylene diamine triacetic acid), methyl cyclodextrin, pentapotassium triphosphate, pentasodium aminotrimethylene phosphonate, pentasodium triphosphate, pentetic acid, phytic acid, potassium citrate, potassium gluconate, sodium citrate, sodium diethylenetriamine pentamethylene phosphonate, sodium dihydroxyethylglycinate, sodium gluconate, sodium metaphosphate, sodium metasilicate, sodium phytate, triethanolamine ("TEA")-EDTA, TEA-polyphosphate, tetrahydroxypropyl ethylenediamine, tetrapotassium pyrophosphate, tetrasodium EDTA, tetrasodium pyrophosphate, tripotassium EDTA, trisodium EDTA, trisodium HEDTA, trisodium phosphate, and the like.

Embodiments of the invention can also include one or more materials that can function as a humectant. A humectant is added to a composition to retard moisture loss during use, which effect is accomplished, in general, by the presence therein of hygroscopic materials.

In some other embodiments, each compound can make up between about 1% to about 99%, by weight (wt/wt %) or by volume (vol/vol %), of the composition. For example, one composition of the present invention comprises about 5% geraniol and about 10% lauric acid (dodecanoic acid). As used herein, percent amounts, by weight or by volume, of compounds are to be understood as referring to relative amounts of the compounds. As such, for example, a composition including 7% linalool, 35% thymol, 4% alpha-pinene, 30% para-cymene, and 24% soy bean oil (vol/vol %) can be said to include a ratio of 7 to 35 to 4 to 30 to 24 linalool, thymol, alpha-pinene, para-cymene, and soybean oil, respectively (by volume). As such, if one compound is removed from the composition, or additional compounds or other ingredients are added to the composition, it is contemplated that the remaining compounds can be provided in the same relative amounts. For example, if soybean oil were removed from the exemplary composition, the resulting composition would include 7 to 35 to 4 to 40 linalool, thymol, alpha-pinene, and para-cymene, respectively (by volume). This resulting composition would include 9.21% linalool, 46.05% thymol, 5.26% alpha-pinene, and 39.48% para-cymene (vol/vol %). For another example, if safflower oil were added to the original composition to yield a final composition containing 40% (vol/vol) safflower oil, then the resulting composition would include 4.2% linalool, 21% thymol, 2.4% alpha-pinene, 18% para-cymene, 14.4% soy bean oil, and 40% safflower oil (vol/vol %). One having ordinary skill in the art would understand that volume percentages are easily converted to weight percentages based on the known or measured specific gravity of the substance.

In certain embodiments, it can be desirable to include a naturally-occurring version or a synthetic version of a compound. In certain exemplary compositions, it can be desirable to include a compound that is designated as meeting Food Chemical Codex (FCC), for example, Geraniol Fine FCC or Tetrahydrolinalool FCC, which compounds can be obtained, for example, from Renessenz LLC.

In certain embodiments, it can be desirable to combine an arthropod control blend as described herein with a synthetic insecticide such as pyrethroid compound, a nitroguanidine compound or a chloronicotinyl compound. For example, in certain embodiments it can be desirable to combine a blend with delatamethrin, clothianidin or imidacloprid, or a combination thereof. Delatamethrin is available for example from AgrEvo Environmental Health, Inc., of Montvale, N.J. Clothianidin and imidacloprid are available from Bayer CropScience LP of Research Triangle Park, N.C.

In embodiments of the invention that include at least one blend of compounds of a plant origin, the compounds of plant origin can be tested for their precise chemical composition using, for example, High-Pressure Liquid Chromatography (HPLC), Mass Spectrometry (MS), gas chromatography, or the like.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "substantially," as used herein, means at least about 80%, preferably at least about 90%, more preferably at least about 99%, for example at least about 99.9%. In some embodiments, the term "substantially" can mean completely, or about 100%.

Embodiments of the invention can include at least one oil, such as, for example, "Superior oil," highly-refined oils, and the like.

"Disablement" is an effect wherein arthropods are mobility-impaired such that their mobility is reduced as compared to arthropods that have not been exposed to the composition. In some embodiments, disablement is an effect wherein at least about 75% of arthropods are mobility-impaired such that their mobility is reduced as compared to arthropods that have not been exposed to the composition. In some embodiments, disablement is an effect wherein at least about 90% of arthropods are mobility-impaired such that their mobility is reduced as compared to arthropods that have not been exposed to the composition. In some embodiments, disablement can be caused by a disabling effect at the cellular or whole-organism level.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Mosquito Arm-in-Cage Studies

An *Aedes aegypti* colony was established from eggs kindly provided by the USDA (Gainesville, Fla.) in 2007. The colony was supplemented with mosquitoes purchased as larvae from Benzon Research (Carlisle, Pa.) in 2012 to maintain genetic diversity. Larvae were fed 1:1 fish food:rat chow and adults were provided 10% sucrose solution and water ad libitum. Adult *An. quadrimaculatus* were generously provided by Charles Apperson from colonies reared at North Carolina State University (Raleigh, N.C.). *Culex quinquefasciatus* were purchased as pupae from Benzon Research. Mosquitoes were maintained in an insectary at 80±2° C., ≈55% RH, and a photoperiod of 12:12 (L:D) h. Adult females used in repellency bioassays were fed 10% sucrose solution and water ad libitum prior to experiments and were never provided a bloodmeal. All mosquitoes were certified to be disease free. Tests using *Ae. aegypti* and *An. quadrimaculatus* were conducted between 09:00 and 17:00. *Culex quinquefasciatus* trials were run between 18:00 and 23:00.

Test substances and their active ingredients are listed in Table 1. All test substances with the exception of TT-4228, TT-4229, and TT-4302 were purchased from retail stores in 2012. TT-4228, TT-4229, and TT-4302 were formulated at TyraTech. Test substances were applied to human skin at a rate of 1 ml/600 cm$^2$. Test substances were chosen to represent a range of active ingredients, both synthetic and of natural origin. Test substances were aliquoted into separate 22 mL amber-colored glass vials and were assigned numbers to ensure blinding from the study conductor and test subjects. Repellents were then randomly assigned by number to volunteers each test day. For *An. quadrimaculatus* trials, TT-4302 and OFF! Active (15% deet) were tested.

TABLE 1

Products tested in arm-in-cage repellency bioassays against *Aedes aegypti*.

| Name | Ingredient(s) from Product Label | Manufacturer | Label Claimed Duration and Target Arthropods |
|---|---|---|---|
| Badger anti-bug | Soybean oil (23%), castor oil (10%), citronella (4%), cedar oil (2%), lemongrass (2%), rosemary oil (1.5%), geranium oil (1%), peppermint oil (1%), other ingredients: water (55.5%), wintergreen (0.5%) | W.S. Badger Company, Inc. | Tested to repel mosquitoes |
| BioUD | 2-Undecanone (7.75%), other ingredients (92.25%) | HOMS, LLC, Clayton, NC | Repels mosquitoes, ticks, and other arthropods |
| Bite Blocker Xtreme | Soybean oil (3%), geranium oil (6%), castor oil (8%), other ingredients (water, coconut oil, glycerin, lecithin, wintergreen oil, citric acid, sodium bicarbonate, benzoic acid) (83%) | HOMS, LLC, Clayton, NC | Repels mosquitoes and black flies for up to 8 h; ticks for up to 2 h; gnats and fleas |

TABLE 1-continued

Products tested in arm-in-cage repellency bioassays against *Aedes aegypti*.

| Name | Ingredient(s) from Product Label | Manufacturer | Label Claimed Duration and Target Arthropods |
|---|---|---|---|
| Burt's Bees Herbal Insect Repellent | Castor oil (10%), rosemary oil (3.77%), lemongrass oil (2.83%), cedar oil (0.94%), peppermint oil (0.76%), citronella oil (0.57%), clove oil (0.38%), geranium oil (0.19%), other ingredients (soybean oil, vitamin E) (80.56%) | Burt's Bees, Inc., Durham, NC | none |
| Buzz Away Extreme | Castor oil (8%), geranium oil (6%), soybean oil (3%), cedarwood oil (1.5%), citronella oil (1%), peppermint oil (0.5%), lemongrass oil (0.25%), other ingredients (water, coconut oil, glycerin, lecithin, sodium bicarbonate, citric acid, sodium benzoate, wintergreen oil) (79.75%) | Quantum, Inc., Eugene, OR | Repels mosquitoes for up to 4 h |
| California Baby | Citronella (5%), lemongrass (0.5%), cedar (0.5%), other ingredients (water, lecithin, soap bark exract, vegetable glycerin) (94%) | Honky Tots, Inc., Los Angeles, CA | Repels mosquitoes, fleas, ticks, and biting flies |
| Cutter Advanced | Picaridin (7%), other ingredients (93%) | Spectrum, United Industries Corp., St. Louis, MO | Repels mosquitoes |
| Cutter Natural | Geraniol (5%), soybean oil (2%), sodium laurel sulfate (0.4%), potassium sorbate (0.1%), other ingredients (water, vanillin, glycerin, xanthan gum, citric acid) (92.5%) | Spectrum, United Industries Corp., St. Louis, MO | Repels mosquitoes for up to 2 h |
| Deter | Soybean oil (22%), spearmint oil (10%), geraniol (4%), geranium oil (1%), other ingredients (coconut oil, celery seed oil, vanillin, vitamin E, BHT) (63%) | Mariner Biomedical, Inc., San Jose, CA | Repels mosquitoes, ticks, gnats, fleas, and black flies for up to 4 h |
| EcoSMART Organic | Geraniol (1%), rosemary oil (0.5%), cinnamon oil (0.5%), lemongrass oil (0.5%), other ingredients (2-propanol, isopropyl myristate, wintergreen oil) (97.5%) | EcoSMART Technologies, Inc., Alpharetta, GA | Repels mosquitoes, ticks, gnats, and other annoying pests for hours |
| TT-4228 | Geraniol (5%), other ingredients (white mineral oil, denatured ethanol, isopropyl myristate, lauric acid, vanillin, triethyl citrate) (95%) | | |
| TT-4229 | Geraniol (5%), other ingredients (white mineral oil, denatured ethanol, isopropyl | | |

TABLE 1-continued

Products tested in arm-in-cage repellency bioassays against *Aedes aegypti*.

| Name | Ingredient(s) from Product Label | Manufacturer | Label Claimed Duration and Target Arthropods |
|---|---|---|---|
| | myristate, lauric acid, vanillin, triethyl citrate, vitamin E) (95%) | | |
| TT-4302 | Geraniol (5%), other ingredients (white mineral oil, isopropyl alcohol, isopropyl myristate, lauric acid, vanillin, triethyl citrate, vitamin E) (95%) | | |
| Kids Herbal Armor | Soybean oil (11.5%), citronella oil (10%), peppermint oil (2%), cedar oil (1.5%), lemongrass oil (1%), geranium oil (0.05%), other ingredients (water, glyceryl stearate, beeswax, vegetable glycerine, xanthan gum, potassium sorbate, citric acid) (73.95%) | All Terrain ®, Rosemont Ventures, Inc., Sunapee, NH | Insects |
| Off! Active | Deet (15%), other ingredients (85%) | SC Johnson & Son, Inc., Racine, WI | Provides hours of effective protection from mosquitoes, gnats, and biting flies (sand flies, stable flies, and black flies). Also repels ticks, chiggers, and fleas from treated skin and clothing. |
| Off! Botanicals lotion | p-Menthane-3,8-diol (10%), other ingredients (90%) | SC Johnson & Son, Inc., Racine, WI | Repels mosquitoes, black flies, gnats, no-see-ums, chiggers, and ticks |
| Off! Botanicals spray | p-Menthane-3,8-diol (10%), other ingredients (90%) | SC Johnson & Son, Inc., Racine, WI | Repels mosquitoes, black flies, gnats, no-see-ums, and ticks up to 2 h |
| Off! Familycare | Deet (7%), other ingredients (93%) | SC Johnson & Son, Inc., Racine, WI | Repels mosquitoes, biting flies, ticks, gnats, no-see-ums, and chiggers up to 2 h |
| Coleman SkinSmart | 3-(N-Butyl-N-acetyl)-amino propionic acid ethyl ester (20%), other ingredients (80%) | Wisconsin Pharmacal Co., LLC, Jackson, WI | Repels mosquitoes and ticks up to 8 h |

All human volunteers provided written informed consent before beginning the study. The testing protocol was adapted from the Environmental Protection Agency's (EPA) Product Performance Test Guidelines Insect Repellents to be applied to Human Skin (2010). The test area was the volunteer's forearm from the elbow to the wrist. Before repellent application, the test area was sprayed with 70% ethanol until thoroughly damp and then dried with a clean paper towel. One arm was treated with a test substance and the other remained untreated, serving as the control. Control arms were cleansed using the same method. During testing, white latex gloves were worn to protect the hands from mosquito bites.

For each test, eighty nulliparous, host-seeking adult female mosquitoes aged 5-10 d were placed in a square 45.7×45.7×45.7 cm cage with a sleeved opening at the front for insertion of the volunteer's forearm. On each testing day, each subject used a separate test cage containing naïve mosquitoes. Landing counts were taken at 30 min intervals beginning 30 min after repellent application until ≤90% repellency was achieved. A landing was defined as a mosquito resting on the surface of the volunteer's arm for ≥2 s. At each testing time point, the control arm was inserted into the cage and the number of landings was recorded by the study conductor for 1 min. The treated arm was then inserted for the same time period and the number of landings was recorded. The same observer recorded landings for all tests and instructed volunteers to move the arm periodically to avoid blood-feeding. The landing count minimum was five mosquitoes per minute on the control arm. Test procedures were repeated four times using four different volunteers for a given test substance.

Percentage repellency was calculated as (control count−treatment count/control count)×100.

*Aedes aegypti* Separate one-way ANOVAs (SAS Institute, 2000-2004), were carried out for each evaluation time on percent repellency and on arc sine transformed values. After time 1, these ANOVAs were unbalanced because any replicate that had failed at an earlier time was not reevaluated. Means for repellents were compared using Fisher's protected LSD at significance level 0.05.

*Anopheles quadrimaculatus* Percent repellency data were arc sine transformed prior to analysis using separate one-way ANOVAs for each evaluation time point. Mean repellency for TT-4302 versus 15% deet were compared for each time point and across all time points using Fisher's protected LSD with a significance level of 0.05 (SAS Institute, 2000-2004) (FIG. 1).

Example 2

Comparative Repellency of Seventeen Mosquito Repellents in Arm-in-Cage Trials Seventeen repellent products, including the novel plant-based repellent TT-4302 and a 15% deet product (positive control) were compared in arm-in-cage studies against *Ae. aegypti*. Mean percentage repellency data, standard errors and LSD groupings for *Ae. aegypti* are presented for each evaluation time in Table 2. Statistically significant differences between repellents were noted for evaluations at 0.5 (F=23.27; df=16, 51; P<0.001), 1 (F=4.57; df=11, 26; P<0.001), 2 (F=6.93; df=9, 20; P<0.001), and 2.5 hr (F=3.66; df=5, 12; P<0.03) after repellent application.

TABLE 2A

Mean percentage repellency (±1 SEM) of commercially available arthropod repellents tested against *Aedes aegypti* in arm-in-cage studies (n = 4 human volunteers per treatment). Values followed by the same letter(s) within the same column (time point) are not statistically significantly different from one another (P ≤ 0.05).

| | \multicolumn{10}{c}{Time (h)} | | | | | | | | | |
|---|---|---|---|---|---|---|---|---|---|---|
| | 0.5 | 1.0 | 1.5 | 2.0 | 2.5 | 3.0 | 3.5 | 4.0 | 4.5 | 5.0 |
| Badger | 84.0 ± 1.9 efg | | | | | | | | | |
| BioUD | 88.3 ± 2.7 defg | | | | | | | | | |
| BiteBlocker | 98.2 ± 0.5 abc | 93.8 ± 1.8 cd | 91.3 ± 3.6 cde | | | | | | | |
| Burt's Bees | 78.2 ± 6.2 fg | | | | | | | | | |
| Buzz Away | 96.0 ± 0.9 abcd | 91.1 ± 1.9 d | 83.6 ± 1.5 e | | | | | | | |
| CA Baby | 34.9 ± 11.0 h | | | | | | | | | |
| Cutter Advanced | 93.4 ± 2.4 bcde | | | | | | | | | |
| Cutter Natural | 47.4 ± 13.4 h | | | | | | | | | |
| Deter | 95.8 ± 3.0 abcd | 95.7 ± 0.7 bcd | 94.2 ± 0.8 cd | 85.3 ± 1.8 c | | | | | | |
| EcoSMART | 12.0 ± 9.5 i | | | | | | | | | |
| TT-4228 | 99.7 ± 0.35 a | 98.4 ± 1.7 a | 98.2 ± 0.8 a | 99.3 ± 0.5 a | 97.5 ± 0.6 ab | 97.0 ± 1.1 a | 91.8 ± 4.0 a | 90.9 ± 3.7 | | |
| TT-4302 | 99.9 ± 0.2 a | 99.7 ± 0.2 a | 99.7 ± 0.3 a | 99.5 ± 0.5 a | 98.8 ± 0.3 ab | 96.9 ± 1.6 a | 97.1 ± 1.4 a | 97.3 ± 1.6 | 96.4 ± 1.0 | 94.7 ± 2.5 |
| Herbal Armor | 71.7 ± 7.3 g | | | | | | | | | |
| OFF! Active | 99.3 ± 0.7 ab | 99.1 ± 0.7 ab | 98.9 ± 0.8 ab | 98.2 ± 1.2 ab | 96.3 ± 2.3 ab | 96.3 ± 1.7 a | 88.5 ± 3.0 a | | | |
| OFF! Botanicals lotion | 96.8 ± 1.1 abcd | 93.3 ± 2.1 cd | 84.2 ± 3.0 de | | | | | | | |
| OFF! Botanicals spray | 98.9 ± 0.8 ab | 97.9 ± 1.0 abc | 96.0 ± 1.6 bc | 85.5 ± 5.6 c | | | | | | |
| OFF! Familycare | 99.0 ± 1.2 ab | 93.4 ± 3.1 cd | 90.9 ± 5.0 cde | | | | | | | |
| SkinSmart | 88.7 ± 3.9 cdef | | | | | | | | | |

TABLE 2B

Mean number of mosquitoes (±1 SEM) per minute landing on untreated forearms during arm-in-cage trials using *Ae. aegypti* (n = 4 human volunteers per treatment).

| | Time (h) | | | | | | | | | |
|---|---|---|---|---|---|---|---|---|---|---|
| | 0.5 | 1.0 | 1.5 | 2.0 | 2.5 | 3.0 | 3.5 | 4.0 | 4.5 | 5.0 |
| Badger | 120.0 ± 19.2 | | | | | | | | | |
| BioUD | 149.5 ± 26.8 | | | | | | | | | |
| BiteBlocker | 192.8 ± 10.2 | 154.3 ± 24.1 | 151.7 ± 42.8 | | | | | | | |
| Burt's Bees | 161.0 ± 18.8 | | | | | | | | | |
| Buzz Away | 121.3 ± 13.0 | 140.0 ± 22.7 | 128.3 ± 28.6 | | | | | | | |

TABLE 2B-continued

Mean number of mosquitoes (±1 SEM) per minute landing on untreated forearms during arm-in-cage trials using *Ae. aegypti* (n = 4 human volunteers per treatment).

| | Time (h) | | | | | | | | | |
|---|---|---|---|---|---|---|---|---|---|---|
| | 0.5 | 1.0 | 1.5 | 2.0 | 2.5 | 3.0 | 3.5 | 4.0 | 4.5 | 5.0 |
| CA Baby | 181.5 ± 20.3 | | | | | | | | | |
| Cutter Advanced | 158.5 ± 37.6 | | | | | | | | | |
| Cutter Natural | 115.5 ± 29.2 | | | | | | | | | |
| Deter | 190.3 ± 19.2 | 135.7 ± 27.7 | 136.7 ± 37.9 | 141.3 ± 30.0 | | | | | | |
| EcoSMART | 134.3 ± 21.7 | | | | | | | | | |
| Herbal Armor | 208.3 ± 28.8 | | | | | | | | | |
| OFF! Active | 91.5 ± 41.4 | 101.8 ± 48.4 | 105.8 ± 37.2 | 127.0 ± 47.6 | 134.3 ± 58.0 | 116.7 ± 57.1 | 119.7 ± 67.9 | | | |
| OFF! Botanicals lotion | 154.3 ± 6.4 | 141.8 ± 15.1 | 147.0 ± 18.8 | 134.8 ± 20.5 | | | | | | |
| OFF! Botanicals spray | 151.3 ± 28.2 | 126.0 ± 22.1 | 118.7 ± 16.8 | | | | | | | |
| OFF! Family care | 99.0 ± 1.2 | 93.4 ± 3.1 | 90.9 ± 5.0 | | | | | | | |
| SkinSmart | 162.5 ± 39.2 | | | | | | | | | |
| TT-4302 | 156.3 ± 33.7 | 145.3 ± 26.1 | 137.3 ± 16.0 | 116.3 ± 23.2 | 124.0 ± 18.5 | 123.0 ± 20.5 | 125.3 ± 12.7 | 155.3 ± 36.4 | 140.8 ± 31.8 | 180.5 ± 8.1 |

Eight repellents (Badger, BioUD, Burt's bees, California Baby, Cutter Natural, EcoSMART, Herbal Armor, and SkinSmart) exhibited a mean repellency below 90% to *Ae. aegypti* at 0.5 h after application. At the first evaluation time point (30 min after repellent application), all replicates failed (<90% repellency) for the repellents CA Baby, Cutter Natural, EcoSMART, and Herbal Armor. The highest mean repellency observed was for TT-4302 (99.8%). Repellency of TT-4302 was statistically significantly different from Badger, BioUD, Burt's Bees, CA Baby, Cutter Advanced, Cutter Natural, EcoSMART, Herbal Armor and SkinSmart. OFF! Active, OFF! Botanicals spray, and OFF! Familycare, also had high observed repellencies (99.3, 98.8, and 99.0%, respectively), and were each significantly higher than Badger, BioUD, Burt's Bees, CA Baby, Cutter Natural, EcoSMART, Herbal Armor, and SkinSmart. BiteBlocker (98.2% repellency) had significantly greater repellency than Badger, BioUD, Burt's Bees, Cutter Natural, CA Baby, EcoSMART, and Herbal Armor. The top five, TT-4302, OFF! Active, OFF! Familycare, OFF! Botanicals spray and BiteBlocker, did not differ significantly at the 30 min evaluation (Table 2).

Three repellents (Buzz Away Extreme, Cutter Advanced, and OFF! Botanicals lotion) fell below 90% repellency 1.5 h after application. At the 1 h and 1.5 h evaluations, TT-4302, OFF! Active and OFF! Botanicals spray had the highest observed mean repellencies (Table 2) and repellency was >90% for all replicates. At the 1 h time point, these three repellents did not differ significantly. At 1.5 h after repellent application, TT-4302 had significantly higher repellency than all other repellents except OFF! Active.

At the 2 h evaluation, TT-4302 and OFF! Active were the only repellents for which all 4 replicates were found to be effective. One replicate for OFF! Botanicals spray and 2 replicates for OFF! Active persisted until 4 h, and all replicates of TT-4302 remained effective through the 4.5 h evaluation. The difference between TT-4302 and OFF! Active was not significant based on ANOVAs performed on repellency for the decreasing number of replicates at the 2-3.5 h evaluations, but TT-4302 (4 replicates) had significantly greater repellency than OFF! Active (2 replicates) at the 4 h evaluation. At 4.5 and 5 h, only TT-4302 replicates remained effective with mean percentage repellencies of 96.4% and 94.7%, respectively (FIG. 1).

Example 3

Comparative Repellency of TT-4302 and Deet Against *Anopheles quadrimaculatus*

A comparison of the repellency of TT-4302 and 15% deet (OFF! Active) was made against *An. quadrimaculatus* using arm-in-cage trials. Repellency did not differ among TT-4302 and deet from 0.5-5 h after treatment. At 6 h after treatment, TT-4302 provided 95.2% repellency while deet exhibited 72.2%. TT-4302 exhibited greater repellency than deet at the 5.5 (t=3.22; df=1, 6; P=0.02) and 6 h (t=4.50; df=1, 5; P=0.01) time points (FIG. 1).

Example 4

Mosquito Field Trials

Two test compounds were compared in mosquito repellency field trials: TT-4228 or TT-4302 (TyraTech, Inc., Morrisville, N.C.) and OFF! Active (15% deet, SC Johnson & Son, Inc., Racine, Wis.). Test substances were applied to human skin at a rate of 1 ml/600 cm$^2$. The first study examined repellency of TT-4228 and deet applied to the arms of human volunteers. The second study examined repellency of TT-4302 and deet applied to volunteers' legs. In both studies, arms or legs were cleansed and treated as described for mosquito arm-in-cage studies and subjects were randomly assigned a repellent treatment before beginning field trials.

The first repellency trial was conducted in a residential area in Cary, N.C. on 6 and 13 Jun. 2012. All human volunteers provided written informed consent before participating in the study. A total of four replicates for each repellent were conducted. Male to female ratio among volunteers was 5:1.

Test procedures were modified from the EPA's Product Performance Test Guidelines Insect Repellents to be applied to Human Skin (2010) guidance for field studies of mosquito repellency. Subjects wore a mosquito net over the head, long pants, a long-sleeved shirt with the sleeves rolled up to the elbow, and nitrile gloves. Repellents were applied to each volunteer's forearm at 1530 hours (5 h before dusk) and mosquito landing counts began 30 min after repellent application. Volunteers recorded the number of lands on each arm (one treated, one untreated) for five min using hand held mechanical counters. Mean number of lands for the controls for each evaluation period is presented in Table 3. The minimum landing count on the control arm was five mosquitoes in the five minute test period. During testing, volunteers were spaced approx. 4.5 m apart. On each test day, the study conductor collected mosquitoes from subjects using an aspirator. Mosquitoes were returned to the laboratory for identification using the keys of Slaff and Apperson (1989).

TABLE 3

Mean number of mosquitoes (±1 SEM) landing on untreated forearms during field trials in Cary, NC

| Time after application (h) | Mean no. landings on control per 5 min | |
|---|---|---|
| | TT-4228 | Deet |
| 0.5 | 13.7 ± 1.8 | 22.0 ± 2.9 |
| 1 | 15.0 ± 1.2 | 12.8 ± 0.6 |
| 1.5 | 12.0 ± 2.3 | 38.5 ± 9.4 |
| 2 | 18.8 ± 3.1 | 26.0 ± 2.0 |
| 2.5 | 15.0 ± 1.9 | 15.0 ± 2.0 |
| 3 | 16.8 ± 1.3 | 17.0 ± 3.1 |
| 3.5 | 12.2 ± 1.6 | 11.5 ± 1.6 |
| 4 | 8.3 ± 1.0 | 14.3 ± 3.4 |
| 4.5 | 10.7 ± 1.3 | 11.8 ± 2.5 |

A repellency trial was conducted in a residential area in Cary, N.C., USA on 16 Aug. 2012. All human volunteers provided written informed consent before participating in the study. Arms were cleansed and treated as described for mosquito arm-in-cage studies. Subjects were randomly assigned a repellent treatment before beginning field trials. A total of four replicates for each repellent were conducted. Male to female ratio among volunteers was 7:1.

Test procedures were modified from the EPA's Product Performance Test Guidelines Insect Repellents to be applied to Human Skin (2008) guidance for field studies of mosquito repellency. Subjects wore a mosquito net over the head, short pants, a long-sleeved shirt, and nitrile gloves. Repellents were applied to each volunteer's calf between the ankle and knee at 1515 hours (5 h before dusk) and mosquito landing counts began 30 min after repellent application. Volunteers recorded the number of lands on each leg (one treated, one untreated) for five min using hand held mechanical counters. The minimum landing count on the control leg was five mosquitoes in the five minute test period. Mean number of lands for the controls for each evaluation period is presented in Table 4. During testing, volunteers were spaced approx. 4.5 m apart. After each 30 min test interval, the study conductor collected mosquitoes from subjects using an aspirator. Mosquitoes were returned to the laboratory for identification using the keys of Slaff and Apperson (1989).

TABLE 4

Mean number of mosquitoes (±1 SEM) landing on untreated legs during field trials in Cary, NC

| Time after application (h) | Mean no. landings on control per 5 min | |
|---|---|---|
| | TT-4302 | Deet |
| 0.5 | 15.8 ± 2.6 | 37.3 ± 1.0 |
| 1 | 16.5 ± 3.8 | 28.0 ± 3.2 |
| 1.5 | 18.5 ± 1.4 | 21.0 ± 2.9 |
| 2 | 32.3 ± 5.3 | 31.5 ± 3.3 |
| 2.5 | 23.5 ± 3.1 | 27.0 ± 2.8 |
| 3 | 31.8 ± 3.2 | 44.5 ± 7.5 |
| 3.5 | 25.5 ± 2.7 | 31.5 ± 3.6 |
| 4 | 27.0 ± 3.5 | 43.3 ± 4.7 |
| 4.5 | 17.5 ± 4.1 | 31.0 ± 4.1 |
| 5.0 | 5.5 ± 1.2 | 12.5 ± 2.9 |

Percentage repellency for each compound was calculated as: (control count−treatment count/control count)×100. Percentage repellency data were square root transformed to achieve approximate normality and were then analyzed using a repeated measures ANOVA with time as the repeated measure and autoregressive covariance structure (SAS Institute, 2000-2004). Probabilities of differences were calculated in LSD tested for LSM repellencies under the hypothesis $H_0$: $H_i=H_j$ to determine if differences in mean repellency ($P \leq 0.05$) existed between repellents at each time point and across all time points.

TT-4228 and 15% deet (OFF! Active) applied to human arms were compared in the field against wild populations of mosquitoes. The majority of the mosquitoes collected from volunteers were the Asian tiger mosquito, *Aedes albopictus*. *Aedes triseriatus*, the eastern tree hole mosquito, was also collected from volunteers during the study.

Figure 3:
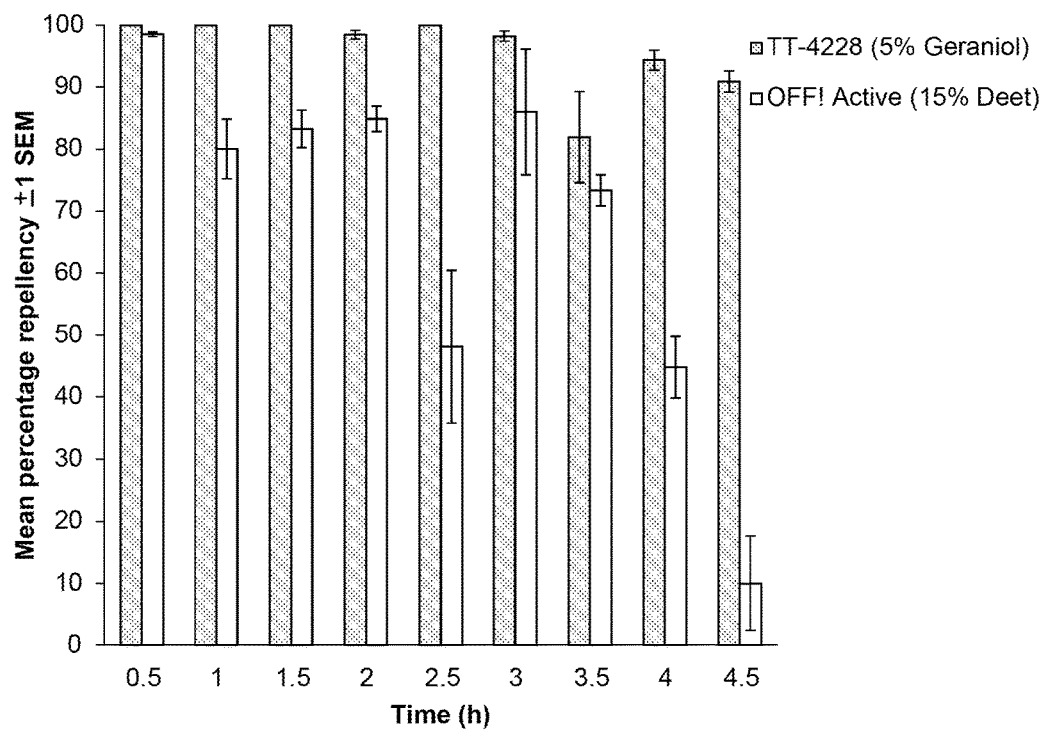
FIG. 3 shows the mean percentage repellency (±1 SEM) of TT-4228 and 15% deet against mosquitoes in the field.

Repellent duration (>90%) of TT-4228 was 4.5 h and exceeded that of deet which failed after the first half hour evaluation point. Repellency of TT-4228 at 4.5 h was 90.8% compared to deet which exhibited only 10% repellency at 4.5 h (FIG. 3).

Figure 4:
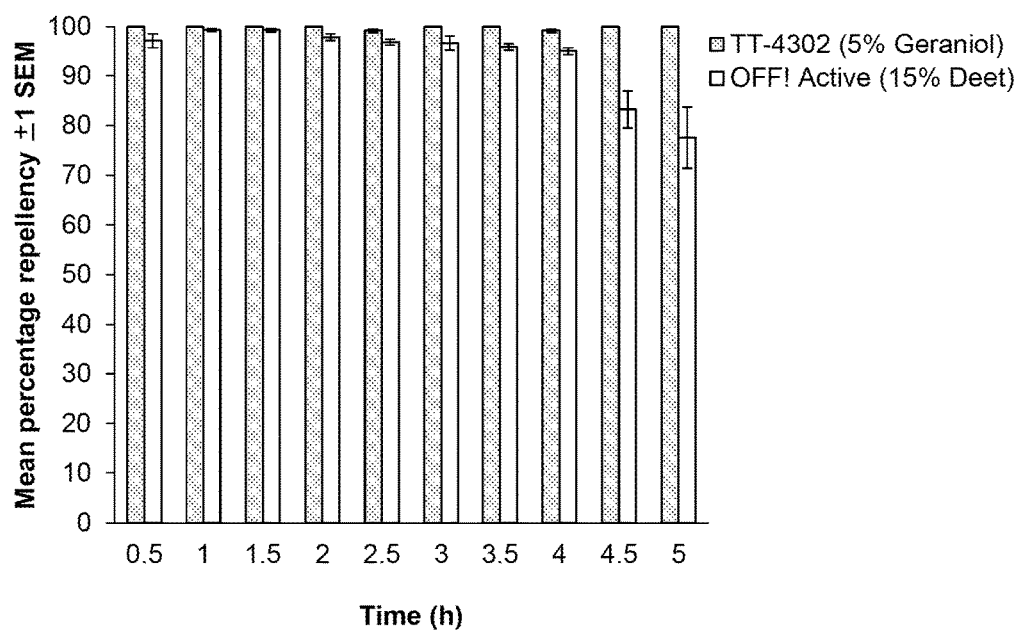
FIG. 4 shows the mean percentage repellency (±1 SEM) of TT-4302 and 15% deet against mosquitoes in the field.

TT-4302 and 15% deet (OFF! Active) applied to human legs were compared in the field against wild populations of mosquitoes. All mosquitoes collected from volunteers were the Asian tiger mosquito, *Aedes albopictus*. Mean percentage repellencies at each testing time point are presented in FIG. 4. No significant difference in mean percentage repellency was observed between TT-4302 and deet (F=1.57; df=1, 4.19; P=0.28). Similarly the effects of time (F=1.36; df=9, 45.7; P=0.23) and the interaction between repellent and time (F=1.57; df=9, 45.7; P=0.15) were not significant. Post hoc LSD tests were not conducted due to the lack of significance in tests of the fixed effects. However, although statistical significance was not observed between TT-4302 and deet 4.5 and 5 h after repellent application, TT-4302 provided 100% repellency at both time points while deet was 83.3% repellent at 4.5 h and 77.6% repellent at 5 h (FIG. 4).

Example 5

Laboratory Tick Studies

Laboratory tick repellency bioassays were conducted with TT-4228, TT-4302 (5% geraniol, TyraTech, Inc., Morrisville, N.C.), and OFF! Active (15% deet, S.C. Johnson and Sons, Inc., Racine, Wis.). Tick field repellency bioassays were conducted with TT-4228 (5% geraniol) and 15% deet. TT-4228 and TT-4302 were formulated at TyraTech and deet was purchased at a local retail store.

Naïve, unfed, adult, host-seeking (as evidenced by raised forelegs in reaction to the investigator's breath), mixed-sex ticks were used in all laboratory bioassays. *Dermacentor variabilis* were kindly provided by D. E. Sonenshine from colonies reared as previously described (Sonenshine 1993) at Old Dominion University, Norfolk, Va. *Amblyomma americanum* were collected from the field in Wake County, N.C., USA on 11 May 2012 and in Chatham County, N.C., USA on 18 May 2012 for trials using TT-4228 and deet. *Amblyomma americanum* for trials using TT-4302 and *I. scapularis* were purchased from the University of Oklahoma Tick Lab (Stillwater, Okla.). *Rhipicephalus sanguineus* were purchased from Ecto Services (Henderson, N.C.). Ticks used in repellency studies were held in plastic vials at 28° C., ~80% RH, with a photoperiod of 15 h light: 9 h dark.

Choice trials were conducted at two different time points after repellent application as previously described by Bissinger et al. (2009) with modifications. Briefly, ticks chose between two (31.8 cm$^2$) semi-circular filter paper (Whatman no. 1) surfaces, one untreated and the other treated with either 250 µL of TT-4228 or deet within a 63.6 cm$^2$ plastic Petri dish lid. Papers were treated in separate glass Petri dishes and were allowed to dry under a fume hood either 2 or 3 h before the beginning bioassays. At the beginning of each bioassay, papers were transferred to separate plastic Petri dish lids and six ticks were positioned along the junction where the treated and untreated surfaces met. An O-ring (3 mm width, 80 mm inner diameter, McMaster-Carr, Robbinsville, N.J.) was placed on top of the papers creating a 3 mm gap between the Petri dish lid and the inverted bottom of the Petri dish thereby allowing ticks to move freely within the arena without being able to turn over or avoid contact with the filter paper substrate. Distribution of ticks was recorded 30 min after introduction of ticks to the arena (2.5 or 3.5 h post repellent treatment). Tests were conducted at 30° C., ~60% RH, under ambient (fluorescent) light. Ticks were allowed to acclimate to testing conditions for 30 min before beginning bioassays.

A chi-squared test for proportions was used to test the null hypothesis that distribution of ticks on filter paper in the absence of a repellent was 0.5 (P=0.05; H$_O$: Proportion=0.5) (PROC FREQ, SAS Version 9.1, SAS Institute, 2000-2004). Percentage repellency was calculated as: (control count-treatment count/control count)×100. Mean percentage repellency data for each tick species were analyzed separately using PROC MIXED in SAS (v. 9.1, SAS Institute 2000-2004) with treatment as the fixed effect. Means separation for repellents and the control was achieved using the protected LSD.

Figure 5:
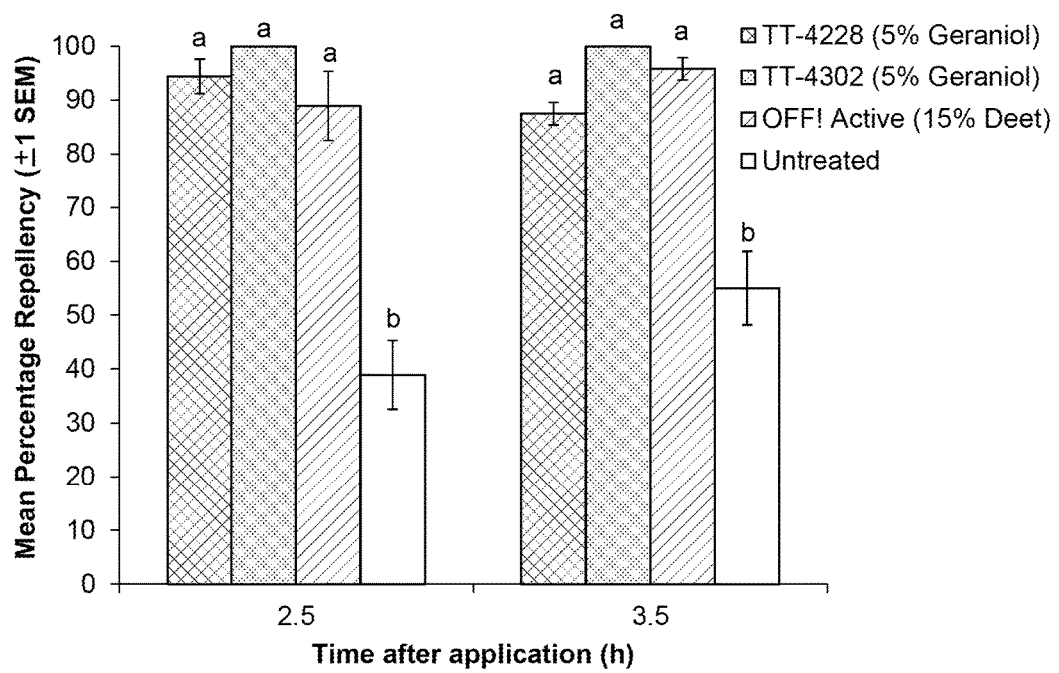
FIG. 5 shows the mean percentage repellency (±1 SEM) of TT-4228, TT-4302, deet, and the untreated control against *A. americanum* 2.5 hours (n=3) and 3.5 hours after application to filter paper paper (n=4). Different letters above bars for the same time point indicate a significant difference in repellency (ANOVA, P<0.05).

Mean percentage repellencies against *A. americanum, D. variabilis, I. scapularis*, and *R. sanguineus* for TT-4302- and deet-treated filter paper compared to untreated filter paper are presented in FIGS. 5-8, respectively. TT-4302 and deet were both significantly repellent (P<0.05) to all species tested at both time points compared to the untreated control in two-choice bioassays. TT-4302 was 100% repellent to *A. americanum* 2.5 h after application. No difference in mean repellency was found between TT-4228 and TT-4302 (t=0.51; df=3, 6; P=0.63), TT-4228 and deet (t=0.51; df=3, 6; P=0.63), or TT-4302 and deet (t=1.02; df=3, 6; P=0.35) 2.5 h after application (FIG. 5). TT-4302 was also 100% repellent against *A. americanum* at 3.5 h after application.

Figure 6:
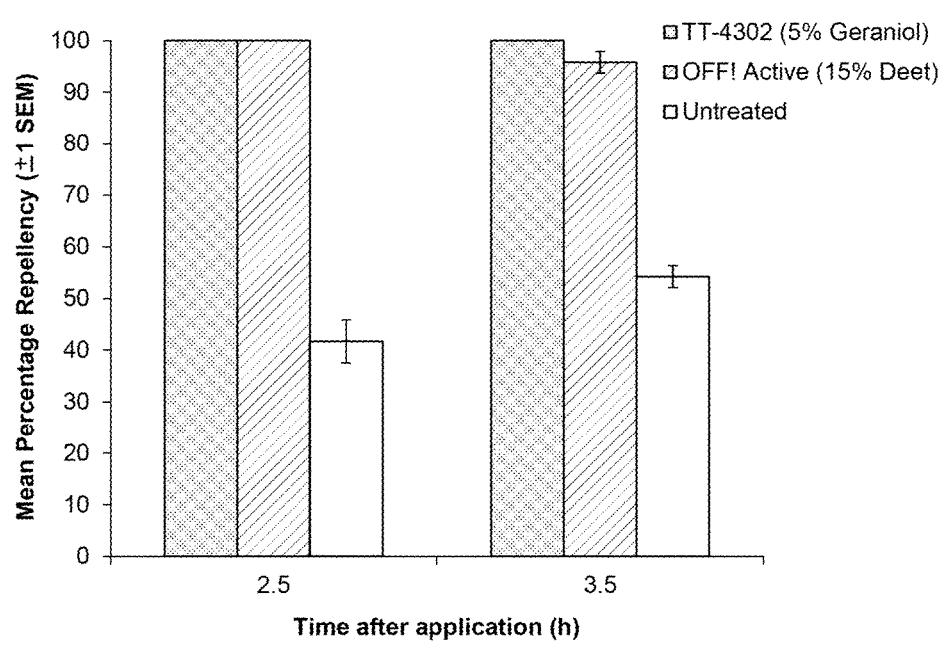
FIG. 6 shows the mean percentage repellency (±1 SEM) of TT-4302, deet, and the untreated control against *D. variabilis* 2.5 hours and 3.5 hours after application to filter paper (n=4). Different letters above bars for the same time point indicate a significant difference in repellency (ANOVA, P<0.05).
Figure 7:
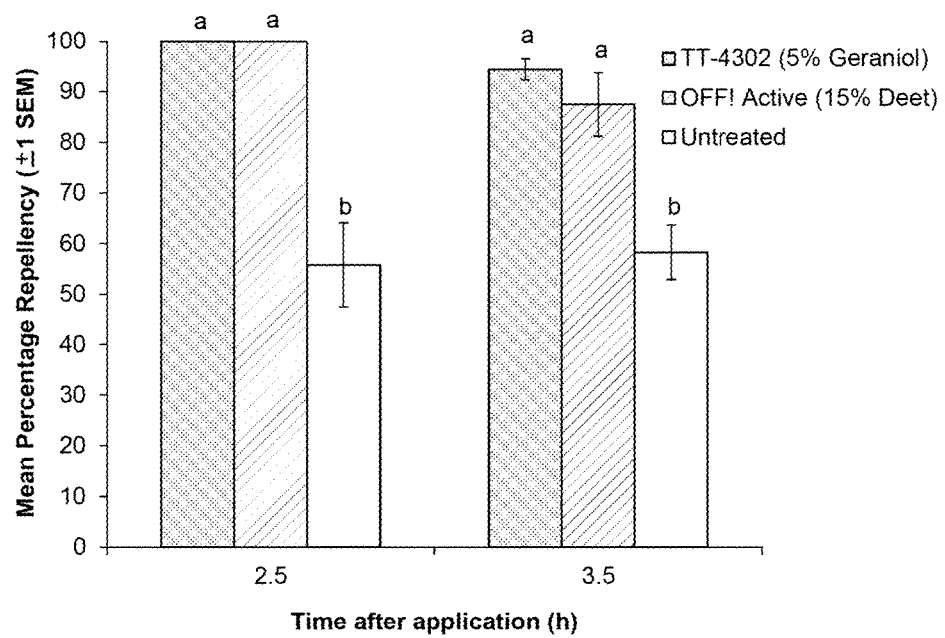
FIG. 7 shows the mean percentage repellency (±1 SEM) of TT-4302, deet, and the untreated control against *I. scapularis* 2.5 hours and 3.5 hours after application to filter paper (n=4). Different letters above bars for the same time point indicate a significant difference in repellency (ANOVA, P<0.05).
Figure 8:
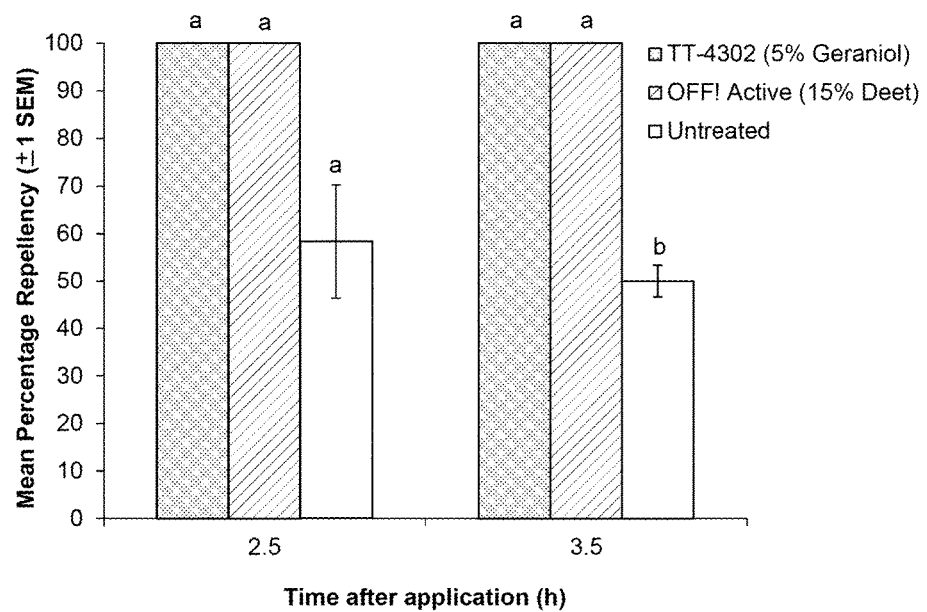
FIG. 8 shows the mean percentage repellency (±1 SEM) of TT-4302, deet, and the untreated control against *R. sanguineus* 2.5 hours and 3.5 hours after application to filter paper (n=4). Different letters above bars for the same time point indicate a significant difference in repellency (ANOVA, P<0.05).

TT-4228 and deet exhibited lower repellency (87.5 and 95.8%, respectively), but this difference was not significantly different from TT-4302 (t=1.20; df=3, 9; P=0.26 and t=0.40; df=3, 9; P=0.70, respectively) nor did TT-4228 and deet differ from one another in repellency (t=0.80; df=3, 9; P=0.44) (FIG. 5). TT-4302 and deet both provided 100% repellency against *D. variabilis* 2.5 h and 3.5 h after application (FIG. 6). TT-4302 and deet both exhibited 100% repellency against *I. scapularis* 2.5 h after application (FIG. 7). No difference in mean percentage repellency was observed between TT-4302 (95.8%) and deet (87.5%) against *I. scapularis* 3.5 h after application (t=0.66; df=2, 6; P=0.53). TT-4302 and deet provided 100% repellency against *R. sanguineus* at both time points (FIG. 8). Distribution of ticks in arenas containing two pieces of untreated filter paper did not differ significantly from 0.5 for *A. americanum* ($\chi^2$=0.89, P=0.35; $\chi^2$=0.39, P=0.53), *D. variabilis* ($\chi^2$=0.39, P=0.53; $\chi^2$=0.67, P=0.41) *I. scapularis* ($\chi^2$=0.39, P=0.53; $\chi^2$=0.67, P=0.41), or *R. sanguineus* ($\chi^2$=0.67, P=0.41; $\chi^2$=0.00, P=1.0) at 2.5 or 3.5 h, respectively.

Example 6

Field Bioassays

Two field bioassays were conducted in a mixed deciduous/coniferous forest with shrubby undergrowth in Chatham County, N.C., USA on 19 and 28 Jun. 2012 following the methods of Bissinger et al. (2011) with modifications. Testing conditions were 31° C., 46% RH on 19 June and 35° C., 86% RH on 28 June. All human volunteers provided written informed consent before participating in bioassays. During testing, volunteers wore shorts that did not extend below the knee, knee high stockings (Hanesbrands, Inc., Winston-Salem, N.C.) (to prevent larval ticks from being able to reach the volunteers' skin), and over-the-calf tube socks (81% cotton, 18% polyester, 1% spandex) (Fruit of the Loom, Inc., Bowling Green, Ky.). Shoes were not worn but insoles were placed inside the stockings to protect the bottoms of the volunteers' feet.

In field trial 1, socks were treated 2.5 h before beginning bioassays. In field trial 2, socks were treated 3.5 h before beginning bioassays. Prior to repellent application, each volunteer placed a sock on their leg and the outer area of the sock was calculated so that the appropriate volume could be applied to socks for each volunteer. Repellents were randomly assigned to volunteers in field trial 1 and then re-assigned in field trial 2 so that each repellent was tested on four different subjects. Five subjects (four male and one female) participated in field trials (four of the five volunteers were involved in testing on a given day).

Repellents were applied at a rate of 1 mL/600 cm$^2$ using separate identical 4 mL glass fingertip pump sprayers (Nemat International, Inc., Fremont, Calif.). Overspray was estimated to be <5%. Socks were hung to dry on a clothesline in a fume hood (with the fan turned off) for 30 min after treatment and then were placed into separate zip top plastic bags for travel to the field. Once in the field, each volunteer placed an untreated sock on one leg and a repellent-treated sock on the other leg. Volunteers were then instructed by the study coordinator to randomly walk at a slow pace (approx. 30 steps/min) over an approx. 5700 m$^2$ area for 15 min. Volunteers were instructed not to follow the same path as one another. During the trial, volunteers removed any ticks that crossed the upper sock barrier and placed them into the appropriate labeled plastic bag for that treatment or control.

After 15 min, volunteers carefully removed the socks and placed them separately into their labeled respective plastic bags which were returned to the laboratory so that the number of ticks on each sock could be recorded. The bioassay was repeated four times each day using two volunteers per repellent treatment (for a total of eight replicates per treatment) keeping the same volunteer for a given treatment and keeping the start time of the assay (2.5 or 3.5 h) constant. Repellent-treated socks were always worn on the same leg of a given subject on the same test day to avoid contamination of the control.

Tick count data for treated versus untreated socks were analyzed by fitting a general linear mixed model to observed responses using PROC MIXED in SAS v. 9.1 (SAS Institute, 2000-2004). Visual examination of scatterplots of predicted versus residual values (Draper and Smith, 1981) showed that residuals were uniformly distributed around a mean of zero, demonstrating that responses displayed homogeneity of variances and normality. Replicate within treatments (repellents and their paired controls) was treated as a random factor. Preplanned pairwise comparisons were conducted to determine if statistically significant differences in the mean number of ticks collected from treated and corresponding control socks existed for each repellent.

Figure 9:
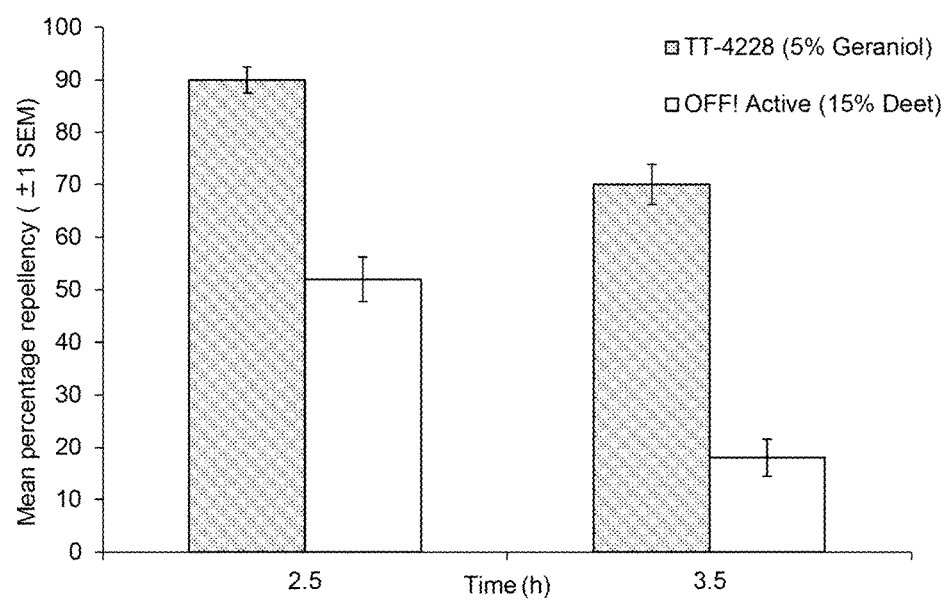
FIG. 9 shows the mean percentage repellency (±1 SEM) of TT-4228 and deet 2.5 hours and 3.5 hours after application to socks against ticks in the field (n=8).

Mean percentage repellency data against ticks for TT-4228 and deet 2.5 and 3.5 h after application to socks are presented in FIG. 9. Mean percentage repellency was significantly greater for socks treated with TT-4228 compared to those treated with deet at the 2.5 (t=2.91, df=1, 14, P=0.01) and 3.5 h (t=3.31, df=1, 12, P=0.006) time points. Significantly fewer ticks were collected from socks treated with TT-4228 (F=22.6, df=1, 28, P<0.0001) and deet (F=13.0, df=1, 28, P=0.001) compared to their paired untreated socks at the 2.5 h time point. Similarly, significantly fewer ticks were collected from TT-4228-treated socks compared to their paired untreated socks (F=19.6, df=1, 24, P=0.0002) at 3.5 h after treatment. However, no significant difference in the number of ticks collected from deet-treated compared to untreated socks was found (F=0.22, df=1, 24, P=0.65) at the same time point. Two species of ticks, *A. americanum* and *D. variabilis*, were collected from socks with the majority of ticks being the former species (98.2% at the 2.5 h time point and 96.6% at the 3.5 h time point). Seventy percent of ticks collected at the 2.5 h time point were nymphs while 61% were nymphs at the 3.5 h time point. Larvae were not counted.

Example 7

Figure 10:
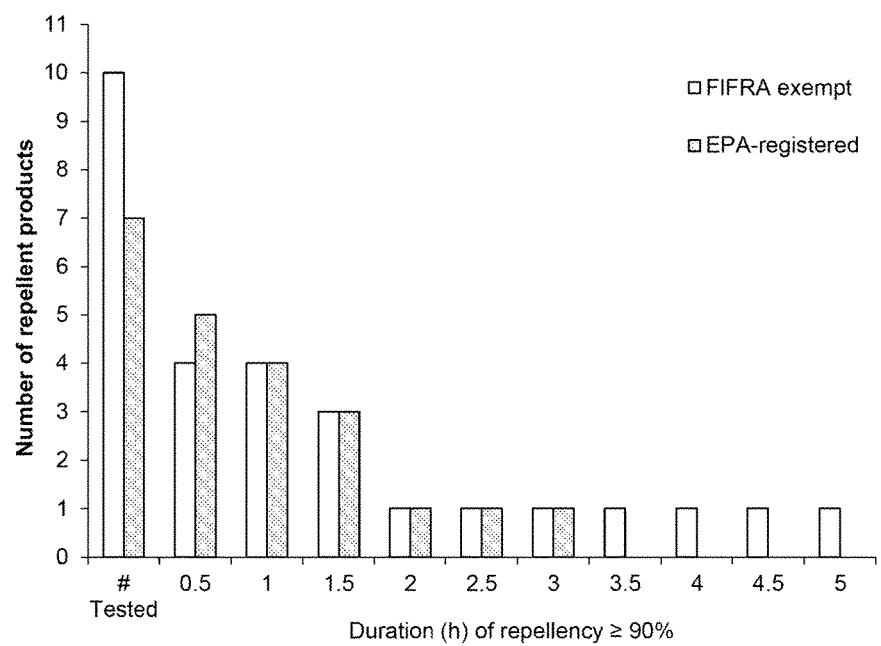
FIG. 10 shows the number of repellent products exhibiting repellency ≥90% at each evaluation time point against *Aedes aegypti* in arm-in-cage bioassays.

Efficacy of FIFRA Exempt Repellents Against *Aedes aegypti* in Arm-in-Cage Trials Seventy percent of commercially available plant-based arthropod repellents contain active and inert ingredients that are considered minimum risk and therefore are exempt from federal regulation (Xue et al. 2007) under a 1996 rule added to FIFRA. While exemption from federal registration allows speed to market, product developers are challenged with designing an efficacious product using a limited list of ingredients. The current study shows the lack of efficacy, at least against *Ae. aegypti*, of several FIFRA exempt repellents (FIG. 10). Six of the ten FIFRA exempt repellents that were tested failed to provide even 30 min of repellency at ≥90%. Only four of the remaining repellents provided protection for at least 1 h and only one, TT-4302, delivered protection for greater than 1.5 h and its performance was maintained for 5 h. Of the seven EPA-registered repellents tested, three (BioUD, IR3535, and Picaridin) provided protection times of 1.5 h or less and one (OFF! Active) delivered 3 h of protection (FIG. 10).

Example 8

Efficacy of F4228 without Lauric Acid

Repellency of F4228 without lauric acid was tested to determine the contribution of lauric acid to the formulation. Bioassays were conducting using *Ae. aegypti* in arm-in-cage trials as discussed previously. F4228 without lauric acid provided 1.5 h of repellency above 95% (mean percent repellency was 95.2% at 1.5 h and 94.4% at 2 h after repellent application). Comparatively, F4228 with lauric acid provided 3 h of repellency above 95%. Lauric acid provides repellent benefit.

Example 9

Efficacy of F4228 without Geraniol and Vanillin

Repellency of F4228 without geraniol and vanillin was tested to determine their contribution to the formulation. Bioassays were conducting using *Ae. aegypti* in arm-in-cage trials as discussed previously. F4228 without geraniol and vanillin provided only 0.5 h of repellency above 95% compared to 3 h when F4228 contained geraniol and vanillin. For the formulation without geraniol and vanillin, mean percent repellency was 96.8% at 30 min and 93.5% at 1 h after repellent application.

Example 10

Laboratory Bed Bug Studies

Laboratory bed bug repellency bioassays were conducted with F4302 (5% geraniol, TyraTech, Inc., Morrisville, N.C.).

Laboratory (insecticide-susceptible Harold Harland and pyrethroid-resistant New Jersey) strains of bed bugs (*Cimex lectularis*) were obtained from laboratory cultures of Coby Schal at North Carolina State University (Raleigh, N.C.). Mixed sex adults were used in all bioassays. Prior to repellency bioassays, bed bugs were held in plastic vials at 27° C., ~55% RH, with a reversed (dark during the day) photoperiod of 12 h light: 12 h dark.

Choice trials were conducted at two different time points after repellent application as previously described by Bissinger et al. (2009) with modifications. Briefly, bed bugs chose between two (31.8 cm$^2$) semi-circular filter paper (Whatman no. 1) surfaces, one untreated and the other treated with either 250 μL of F4302 within a 63.6 cm$^2$ plastic Petri dish lid. Papers were treated in separate glass Petri dishes and were allowed to dry under a chemical fume hood either 3.5 or 23.5 h before the beginning bioassays. Two untreated filter paper halves served as the untreated control to determine distribution of bed bugs in the absence of a repellent. At the beginning of each bioassay, papers were transferred to separate plastic Petri dish lids and four bed bugs were positioned along the junction where the treated and untreated surfaces met. An O-ring (3 mm width, 80 mm inner diameter, McMaster-Carr, Robbinsville, N.J.) was placed on top of the papers creating a 3 mm gap between the Petri dish lid and the inverted bottom of the Petri dish thereby allowing bed bugs to move freely within the arena without being able to turn over or avoid contact with the filter paper substrate. Distribution of bed bugs was recorded 30 min after introduction of bed bugs to the arena (4 or 24 h post repellent treatment). Tests were conducted at 27° C., ~55% RH, in total darkness. Three replicates each were conducted for treatments and controls at both time points.

Figure 11:
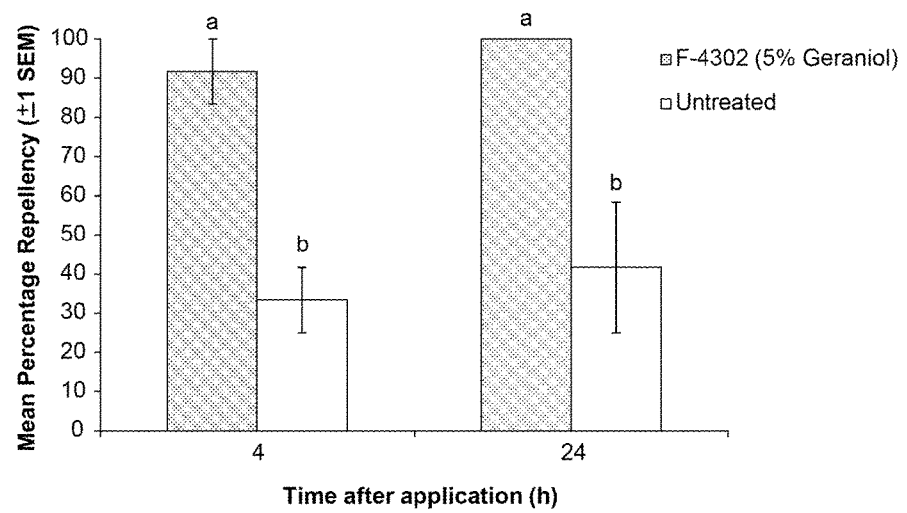
FIG. 11 shows the mean percentage repellency (±1 SEM) of F4302 and the untreated control against insecticide susceptible bed bugs (*Cimex lectularis*) 4 and 24 h after application to filter paper (n=4). Different letters above bars for the same time point indicate a significant difference in repellency (t-test, P<0.05).
Figure 12:
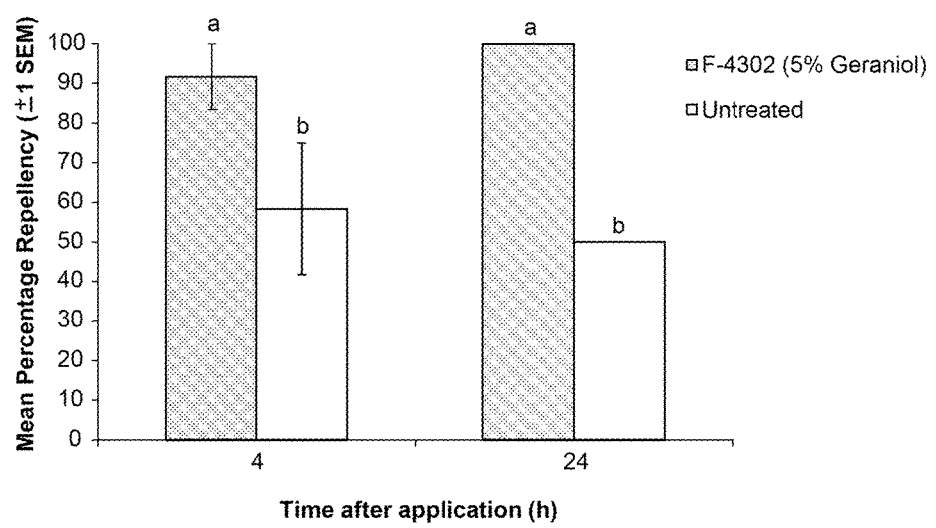
FIG. 12 shows the mean percentage repellency (±1 SEM) of F4302 and the untreated control against pyrethroid-resistant bed bugs (*Cimex lectularis*) 4 and 24 h after application to filter paper (n=4). Different letters above bars for the same time point indicate a significant difference in repellency (t-test, P<0.05).

Mean percentage repellencies of susceptible bed bugs at 4 and 24 h post-treatment of filter paper are presented in FIG. 11. F4302 was 91.7% repellent (11 of the 12 bed bugs were repelled) at 4 h after treatment and 100% repellent 24 h after treatment. Likewise, for pyrethroid-resistant bed bugs, F4302 provided 91.7% repellency 4 h after treatment and 100% repellency at 24 h (FIG. 12).

Example 11

Laboratory Cat Flea Studies

In vitro repellency bioassays using F4302 (5% geraniol, TyraTech, Inc., Morrisville, N.C.) against cat fleas were conducted.

Adult mixed sex cat fleas (*Ctenocephalides felis*) obtained from Ecto Services, Inc (Henderson, N.C.) were used for repellency bioassays. Fleas were held in plastic vials at 27° C., ~55% RH until use in bioassays. Naïve fleas were used in all trials.

Choice tests were conducted at two different time points after repellent application as previously described by Bissinger et al. (2009) with modifications. Briefly, fleas chose between two (31.8 cm$^2$) semi-circular filter paper (Whatman no. 1) surfaces, one untreated and the other treated with 250 µL of F4302 within a 1000 mL glass Pyrex beaker. Papers were treated in separate glass Petri dishes and were allowed to dry under a chemical fume hood either 4 or 23.5 h before beginning the bioassays. Two untreated filter paper halves served as the untreated control to determine distribution of cat fleas in the absence of a repellent. At the beginning of each bioassay, papers were transferred to separate 1000 mL glass Pyrex beakers and 25-30 fleas were added to the beaker. Clear plastic wrap (Great Value, Wal-Mart Stores, Inc., Bentonville, Ark.) was used to cover the beaker to prevent escape. Fleas were allowed to acclimate to the assay conditions for 60 min before data was collected. Distribution of cat fleas on treated and untreated filter papers was recorded by taking a set of 4 photographs (Logitech QuickCam Pro 900w, Newark, Calif.; Webcam XP camera software v 5.5, Moonware Studios), 10 seconds apart, 60 min after introduction of cat fleas to the beaker (5 or 24 h post repellent treatment). Tests were conducted at 24° C., 42% RH, between 0930 and 1630 h. Four replicates each were conducted for treatments and controls at both time points.

Figure 13:
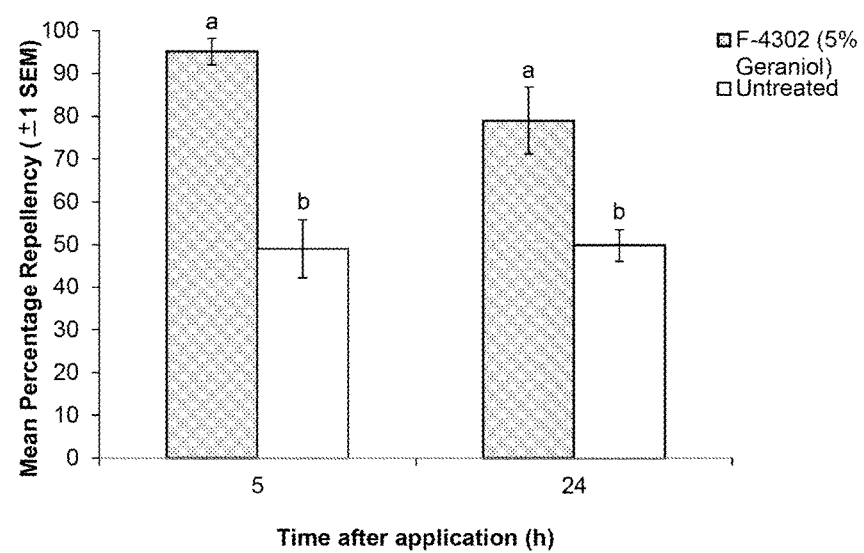
FIG. 13 shows the mean percentage repellency (±1 SEM) of F4302 and the untreated control against cat fleas (*Ctenocephalides felis*) 5 and 24 h after application to filter paper (n=4). Different letters above bars for the same time point indicate a significant difference in repellency (t-test, P<0.05).

Mean percentage repellencies of cat fleas at 5 and 24 h post-treatment of filter paper are presented in FIG. 13. F4302 was 95.1% repellent 5 h after treatment and 49.8% repellent 24 h after treatment.

Example 12

House and Stable Fly Field Trials

Two repellency field trials were conducted at the North Carolina State University (NCSU) Dairy Research and Teaching Farm (Raleigh, N.C.) in October 2012 following the methods of Thomas et al. (1989) with modifications. Protocols for field trials were reviewed and approved by NCSU Institutional Animal Care and Use Committee. Calves were housed individually in molded fiberglass-dome hutches with an adjoining enclosed area constructed from welded-mesh wire. Testing occurred between 1000 and 1700 h with temperatures ranging from 18-27° C. Test substances were applied to the forelegs (from the top of the knee to the top of the phalanges) and rear legs (from top of the hock to the top of the phalanges) of calves (mixed sex, aged 2-56 days old).

Field trial 1 was conducted on 10, 12 and 17 Oct. 2012. Test compounds were TT-4303 (5% geraniol, 2% catnip) (TyraTech, Inc., Morrisville, N.C.) (Table 5) and Bronco E (0.033% prallethrin, 0.1% permethrin, 0.5% piperonyl butoxide) (Farnam, Phoenix, Ariz.). Both treatments were applied using finger-operated, 59 mL pump misters (Paris Presents, Woonsocket, R.I.) that dispensed 0.14 mL per pump. Calf legs were individually treated with 0.84 mL (1 mL/600 cm$^2$) of each treatment. Untreated calves served as negative controls to measure fly pressure in the absence of a repellent.

A randomized (using a random number generator [randomnumber.org]) crossover design was employed so that all calves received both treatments and served as untreated controls over the course of the study. Twelve replicates (8 Holstein and 4 Jersey calves) of each treatment and control were conducted.

The number of flies landing on the legs of calves was recorded for 1 min immediately before treatment and every 30 min from 0.5-3.5 h after treatment. Landings were defined as a fly resting on the calf's leg for ≥2 s. Two observers counted flies during the 1 min observation period; one on either side of the body. All flies observed on the animal were stable flies (*Stomoxys calcitrans*) or the domestic housefly (*Musca domestica*).

Figure 14:
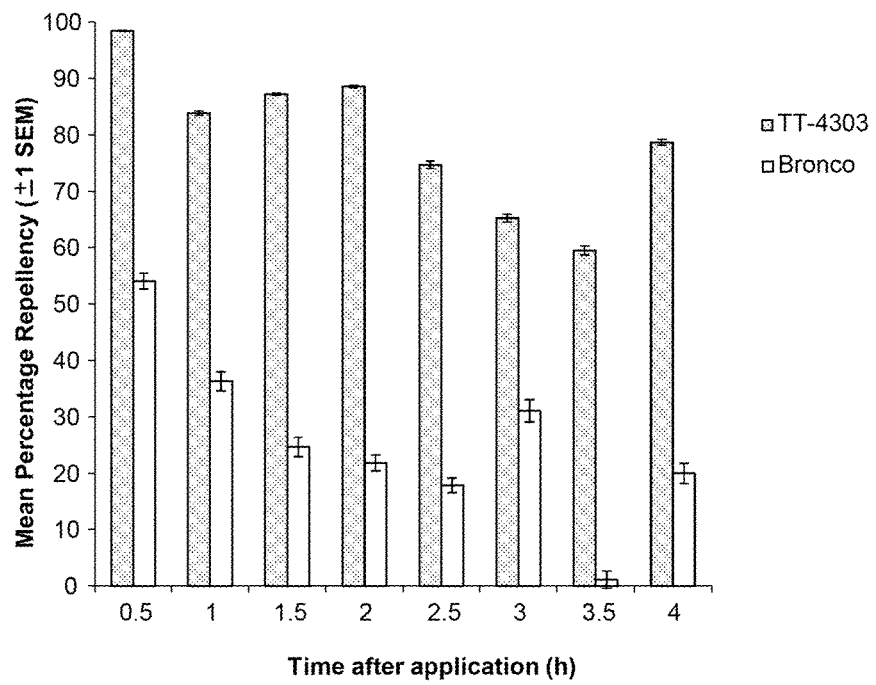
FIG. 14 shows the mean percentage repellency (±1 SEM) of TT-4303 and Bronco E against house and stable flies on calf legs (n=12).

Mean percentage repellency data comparing TT-4303 and Bronco E are presented in FIG. 14. TT-4303 was 88.6% repellent at 2 h post treatment whereas Bronco E was 22% repellent at the same time point. Low repellency of Bronco E is likely due to pyrethroid resistance which was previously documented in flies at the testing site (Hamm et al. 2005). The efficacy of TT-4303 compared to Bronco E demonstrates efficacy of TT-4303 against pyrethroid resistant flies. This efficacy is likely due to TT-4303 having a different mode of action than synthetic pyrethroids.

Repellent application rate (1 mL/600 cm$^2$) in field trial 1 was based on the recommended rate for repellent testing using human subjects. While spraying calves in field trial 1, it was noted that the volume of repellent applied was insufficient to cover the leg of the calf because of the density of hair on the legs and repellent overspray.

In field trail 2, repellent application was increased to 7 mL/600 cm$^2$ (4.1 mL per calf leg). The amount applied was calculated in the laboratory by counting the number of sprays necessary to cover the area (determined by taking the average measured area of the legs from the calves participating in the study) of a calf's leg minus overspray from a spray distance of 6 inches.

Field trial 2 was conducted on 25 Oct. 2012 with TT-4303 (5% geraniol, 2% catnip) (TyraTech, Inc., Morrisville, N.C.) and TT-4304 (5% geraniol, 2% peppermint) (TyraTech, Inc., Morrisville, N.C.) (Table 5). Both treatments were applied using hand-operated pump sprayers that dispensed 1.3 mL per pump. Untreated calves served as negative controls to measure fly pressure in the absence of a repellent. Twelve calves (8 Holstein and 4 Jersey) were randomly assigned to a treatment or control group using a randomized number generator.

One-minute fly landing counts were made immediately before treatment and at 30 min intervals from 2-4 h after treatment. Landings were defined as a fly resting on the calf's leg for ≥2 s. Two observers counted flies during the 1 min observation period; one on either side of the body. All flies observed on the animal were stable flies (*Stomoxys calcitrans*) or the domestic housefly (*Musca domestica*).

Figure 15:
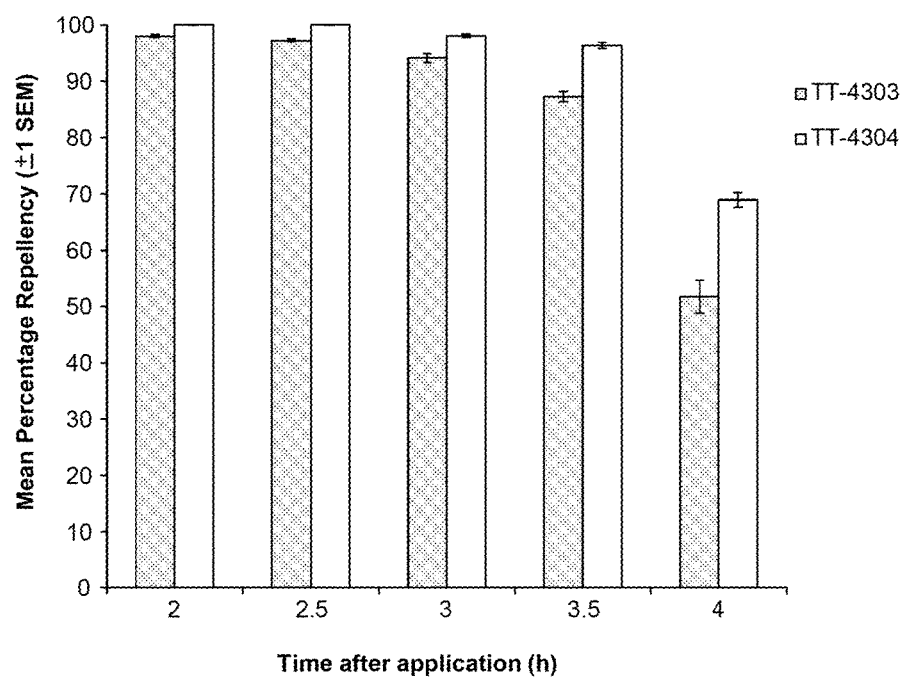
FIG. 15 shows the mean percentage repellency (±1 SEM) of TT-4303 and TT-4304 against house and stable flies on calf legs (n=4).

Mean percentage repellency data for field trail 2 comparing TT-4303 and TT-4304 are presented in FIG. 15. TT-4303 provided 94.8% at 3 h. TT-4304 was 96.4% repellent at 3.5 h. Increasing the application rate of TT-4303 from 1 mL/600 cm$^2$ to 7.75 mL/600 cm$^2$ led to higher repellency for a longer amount of time.

TABLE 5

TyraTech formulations tested against house and/or stable flies.

| Formulation Name | Ingredients |
|---|---|
| TT-4302 | Geraniol (5%), other ingredients (white mineral oil, isopropyl alcohol, isopropyl myristate, lauric acid, vanillin, triethyl citrate, vitamin E) |
| TT-4303 | Geraniol (5%), Catnip (2%), other ingredients (water, glycerin, lauric acid, triethyl citrate, mineral oil, vanillin, isopropyl alcohol, butyl lactate, lanolin, sodium lauryl sulfate) |
| TT-4304 | Geraniol (5%), Peppermint (2%), other ingredients (water, glycerin, lauric acid, triethyl citrate, mineral oil, vanillin, Isopropyl alcohol, butyl lactate, lanolin, sodium lauryl sulfate)(93%) |

Example 13

Mosquito Arm-in-Cage Studies

Equine Repellent

Additional mosquito arm-in-cage studies were conducted using *Aedes aegypti* and human subjects as described in Example 1. These studies were conducted as proof of concept studies for development of an equine fly repellent where humans were used as a surrogate for horses and mosquitoes as surrogates for stable and other biting/nuisance flies.

Test substances and their active ingredients are listed in Table 6. All test substances were formulated at TyraTech. Test substances were applied to human skin at a rate of 1 ml/600 cm$^2$.

TABLE 6

Products tested in arm-in-cage repellency bioassays against *Aedes aegypti*.

| Name | Ingredient(s) |
|---|---|
| TT-4303 | 5% Geraniol, 2% catnip, other ingredients (water, glycerin, lauric acid, triethyl citrate, white mineral oil, vanillin, isopropyl alcohol, butyl lactate, lanolin, sodium lauryl sulfate) (93%) |
| TT-4304 | 5% Geraniol, 2% peppermint (water, glycerin, lauric acid, triethyl citrate, white mineral oil, vanillin, isopropyl alcohol, butyl lactate, lanolin, sodium lauryl sulfate) (93%) |
| TT-4305 | 5% Geraniol, 2% peppermint (water, glycerin, lauric acid, triethyl citrate, white mineral oil, isopropyl alcohol, butyl lactate, lanolin, sodium lauryl sulfate) (93%) |
| TT-4306 | 7% Geraniol (water, glycerin, lauric acid, triethyl citrate, white mineral oil, vanillin, isopropyl alcohol, butyl lactate, lanolin, sodium lauryl sulfate) (93%) |
| TT-4307 | 5% Geraniol, 2% corn mint (water, glycerin, lauric acid, triethyl citrate, white mineral oil, vanillin, isopropyl alcohol, butyl lactate, lanolin, sodium lauryl sulfate) (93%) |

Percentage repellency for each compound was calculated as: (control count−treatment count/control count)×100.

Mean percentage repellency data are presented in Table 7. All repellents tested provided at least 1 h of repellency at ≥95%. TT-4303 provided 94.8% repellency 2.5 h after treatment and TT-4306 was 95.2% repellent 2 h after treatment.

TABLE 7

Mean percentage repellency of TyraTech formulations applied to human forearms against *Aedes aegypti* in arm-in-cage bioassays (n = 3 human subjects per treatment except TT-4303, where n = 4 human subjects).

| Formulation | Time after application (h) | | | | |
|---|---|---|---|---|---|
| | 0.5 | 1.0 | 1.5 | 2.0 | 2.5 |
| TT-4303 | 98.9 ± 0.6 | 99.3 ± 0.0 | 98.4 ± 0.0 | 96.5 ± 2.3 | 94.8 ± 1.0 |
| TT-4304 | 98.0 ± 0.0 | 94.7 ± 0.8 | 93.8 ± 0.3 | | |
| TT-4305 | 96.8 ± 1.6 | 95.6 ± 3.0 | 93.3 ± 1.8 | | |
| TT-4306 | 99.4 ± 0.0 | 96.7 ± 1.8 | 96.8 ± 3.4 | 95.2 ± 0.9 | 86.2 ± 5.7 |
| TT-4307 | 97.8 ± 1.7 | 96.4 ± 2.8 | 90.3 ± 2.8 | | |

Example 14

Laboratory House Fly Studies

In vitro repellency bioassays were conducted against house flies. Repellency of three water-based formulations, TT-4303 (5% geraniol, 2% catnip), TT-4304 (5% geraniol, 2% peppermint), TT-4306 (7% geraniol) was evaluated (Table 8). All repellents were formulated at TyraTech, Inc.

A domestic house fly (*Musca domestica*) colony was established from pupae purchased from Benzon Research (Carlisle, Pa.). Adult house flies were maintained in screened cages with stockinet opening in an insectary at 80±2° C., ≈55% RH, and a photoperiod of 12:12 (L:D) h and are provided sugar water ad libitum prior to repellency testing.

Adult (3-10 day old) mixed sex house flies were used in each repellency bioassay. One hundred flies were anesthetized using $CO_2$, transferred to a 29"×29"×29" cage, and allowed to recover 1 h prior to repellency bioassays. A bait station was positioned in the center of each cage during the recovery period. Bait stations consisted of a cotton ball soaked in 1:1:2 non-dairy creamer:sugar:water mixture in a 2 oz. condiment cup.

Five hundred microliters of each repellent was applied separately to 12.5 cm Whatman no. 1 filter paper with a 5.1 cm hole cut in the center. Filter paper was treated in a glass Petri dish and allowed to dry under a chemical fume hood for 30 min before beginning bioassays. Distilled water served as a control to monitor fly behavior in the absence of a repellent. After the 30 min drying period, treated filter papers were individually attached to a bait station using hot glue. Bait stations with treated filter paper were then placed individually into each bioassay cage.

Repellency of each formulation was evaluated by observing the number of house flies contacting treated or control filter papers or their respective bait stations. Fly contact with filter paper was recorded with a series of 3 consecutive photographs (Logitech QuickCam Pro 900w, Newark, Calif.; Webcam XP camera software v5.5, Moonware Studios) taken 10 seconds apart, every 30 min for 4.5 h after introduction of the treated filter paper into the bioassay cage. Tests conditions ranged between 80-85° F., 25-30% RH, and were conducted between the hours of 0930 and 1730. Three replicates each were conducted for treatments and controls.

Mean percentage repellency for each treatment was calculated based on the water-treated control.

Figure 16:
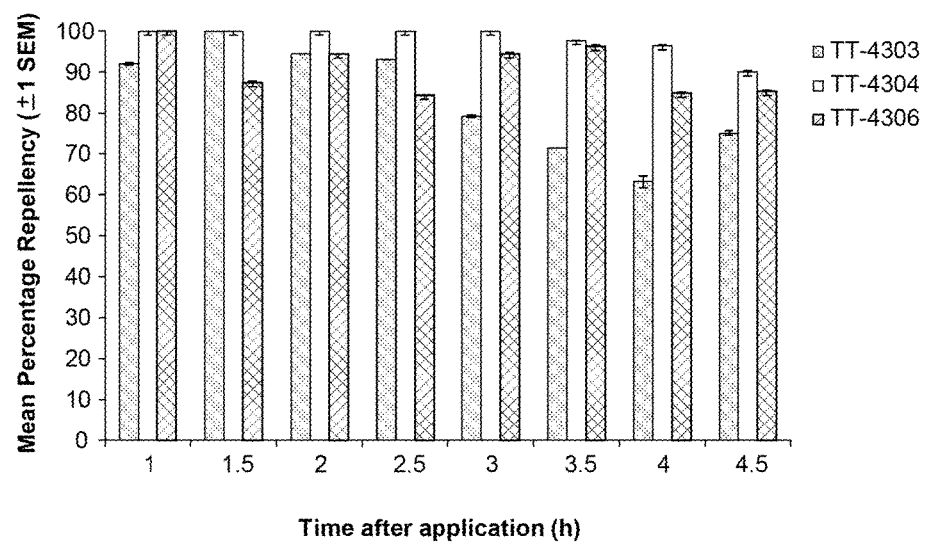
FIG. 16 shows the mean percentage repellency (±1 SEM) of three water-based formulations against domestic house flies (n=3).

Mean percentage repellencies of three water based formulations (±1 SEM) against domestic house flies are presented in FIG. 16. TT-4303 provided 93% repellency 2.5 h after treatment. TT-4304 provided 90.1% repellency 4.5 h after treatment and TT4306 provided 96.3% repellency 3.5 h after treatment.

TABLE 8

TyraTech, formulations tested in house fly bioassay.

| Name | Ingredient(s) |
|---|---|
| TT-4303 | 5% Geraniol, 2% catnip, other ingredients (water, glycerin, lauric acid, triethyl citrate, white mineral oil, vanillin, isopropyl alcohol, butyl lactate, lanolin, sodium lauryl sulfate) (93%) |
| TT-4304 | 5% Geraniol, 2% peppermint (water, glycerin, lauric acid, triethyl citrate, white mineral oil, vanillin, isopropyl alcohol, butyl lactate, lanolin, sodium lauryl sulfate) (93%) |
| TT-4306 | 7% Geraniol (water, glycerin, lauric acid, triethyl citrate, white mineral oil, vanillin, isopropyl alcohol, butyl lactate, lanolin, sodium lauryl sulfate) (93%) |

Tables 9 and 10 contain ingredients and their concentrations of ranges of the blends used in the foregoing examples.

TABLE 9

TyraTech formulations tested.

| | 4228 | 4229 | 4302 | 4303 | 4304 | 4305 | 4306 | 4307 |
|---|---|---|---|---|---|---|---|---|
| geraniol | x | x | x | x | x | x | x | x |
| catnip | | | | x | | | | |
| peppermint | | | | | x | x | | |
| corn mint | | | | | | | | x |
| lauric acid | x | x | x | x | x | x | x | x |
| mineral oil/ white mineral oil | x | x | x | x | x | x | x | x |
| triethyl citrate | x | x | x | x | x | x | x | x |
| vanillin | x | x | x | x | x | | x | x |
| isopropyl myristate | x | x | x | | | | | |
| vitamin E | | x | x | | | | | |
| butyl lactate | | | | x | x | x | x | x |
| lanolin | | | | x | x | x | x | x |
| SLS | | | | x | x | x | x | x |
| isopropyl alcohol | | | x | x | x | x | x | x |
| water | | | | x | x | x | x | x |
| glycerin | | | | x | x | x | x | x |
| denatured EtOH | x | x | | | | | | |

The foregoing specific but non-limiting examples are included herein to illustrate the present invention, but are prophetic, notwithstanding the numerical values, results and/or data referred to and contained therein.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification and Example be considered as exemplary only, and not intended to limit the scope and spirit of the invention.

Unless otherwise indicated, all numbers expressing quantities of ingredients, properties such as reaction conditions, and so forth used in the application are to be understood as being modified in all instances by the term "about." Accordingly, unless indicated to the contrary, the numerical parameters set forth in the application are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

Throughout this application, various publications are referenced. All such references are incorporated herein by reference.

REFERENCES CITED

Aquino, M., M. Fyfe, L. MacDougall and V. Remple 2004. West Nile virus in British Columbia. Emerg. Infect. Dis. 10: 1499-1501.

Barnard, D. R. 1999. Repellency of essential oils to mosquitoes (Diptera: Culicidae). J. Med. Entomol. 36: 625-629.

Bissinger, B. W., C. S. Apperson, D. E. Sonenshine, D. W. Watson and R. M. Roe 2009. Efficacy of the new repellent BioUD® against three species of ixodid ticks. Exp. Appl. Acarol. 48: 239-250

Bissinger, B. W., C. S. Apperson, D. W. Watson, C. Arellano, D. E. Sonenshine and R. M. Roe 2011. Novel field assays and the comparative repellency of BioUD, deet, and permethrin against *Amblyomma americanum*. Med. Vet. Entomol. 25: 217-226

TABLE 10

TyraTech preferred percentages of ingredients.

| | Preferred | Range 1 | | Range 2 | | Range 3 | | Range 4 | | Range 5 | |
|---|---|---|---|---|---|---|---|---|---|---|---|
| geraniol | 5.0% | 0.1 | 10.0 | 1.1 | 9.0 | 2.1 | 8.0 | 3.1 | 7.0 | 4.1 | 6.0 |
| vanillin | 2.5% | 0.0 | 3.0 | 0.5 | 2.9 | 1.0 | 2.8 | 1.5 | 2.7 | 2.0 | 2.6 |
| lauric acid | 10.0% | 2.5 | 20.0 | 4.0 | 18.0 | 5.5 | 16.0 | 7.0 | 14.0 | 8.5 | 12.0 |
| isopropyl myristate | 10.6% | 2.5 | 25.0 | 4.1 | 22.1 | 5.7 | 19.2 | 7.4 | 16.4 | 9.0 | 13.5 |
| mineral oil | 41.5% | 0.0 | 50.0 | 8.3 | 48.3 | 16.6 | 46.6 | 24.9 | 44.9 | 33.2 | 43.2 |
| isopropyl alcohol | 21.1% | 15.0 | 85.0 | 16.2 | 72.2 | 17.4 | 59.4 | 18.7 | 46.7 | 19.9 | 33.9 |
| triethyl citrate | 9.3% | 0.0 | 21.0 | 1.9 | 18.7 | 3.7 | 16.3 | 5.6 | 14.0 | 7.4 | 11.6 |
| vitamin E | 0.1% | 0.1 | 2.5 | 0.1 | 2.0 | 0.1 | 1.5 | 0.1 | 1.1 | 0.1 | 0.6 |

Carroll, J. F., J. P. Benante, J. A. Klun, C. E. White, M. Debboun, J. M. Pound and W. Dheranetra 2008. Twelve-hour duration testing of cream formulations of three repellents against *Amblyomma americanum*. Med. Vet. Entomol. 22: 144-151

Centers for Disease Control and Prevention. 2012 DEET, showers, and tick checks can stop ticks. http://www.cdc.gov/Features/StopTicks/Accessed 19 Jul. 2012

Clem, J. R., D. F. Havemann, and M. A. Raebel 1993. Insect repellent (N, N-diethyl-m-toluamide) cardiovascular toxicity in an adult. Ann. Pharmacother. 27: 289-293.

Draper, N. R. and H. Smith 1981. Applied regression analysis. Wiley, New York

Foster, W. A. and E. D. Walker 2009. Mosquitoes (Culicidae). pp. 207-259. In G. R. Mullen and L. A. Durden [eds.] Medical and veterinary entomology. Elsevier, Burlington, Mass.

Fradin, M. S. and J. F. Day 2002. Comparative efficacy of insect repellents against mosquito bites. N. Engl. J. Med. 347: 13-18.

Frances, S. P. 2007a. Efficacy and safety of products containing deet. pp. 311-326. In M. Debboun, S. Frances, and D. Strickman [eds.] Insect repellents: principles, methods, and uses. CRC, Boca Raton, Fla.

Frances, S. P. 2007b. Picaridin. pp. 337-345. In M. Debboun, S. Frances, and D. Strickman [eds.] Insect repellents: principles, methods, and uses. CRC, Boca Raton, Fla.

Goodyear, L. and R. H. Behrens 1998. Short report: the safety and toxicity of insect repellents. Am. J. Trop. Med. Hyg. 59: 323-324.

Gubler, D. J. and G. G. Clark 1995. Dengue/dengue hemorrhagic fever: the emergence of a global health problem. Emerg. Infect. Dis. 1: 55-57.

Hamm, R. L., T. Shono, and J. G. Scott. 2005. A cline in frequency of autosomal males is not associated with insectide resistance in house fly (Diptera: Muscidae). J. Econ. Entomol. 98: 171-176.

Kimps, N. W., B. W. Bissinger, C. S. Apperson, D. E. Sonenshine and R. M. Roe 2011. First report of the repellency of 2-tridecanone against ticks. Med. Vet. Entomol. 25: 202-208

Masters, E., C. N. Grigery and R. W. Masters 2008. STARI or Masters disease: lone star tick-vectored Lyme-like illness. Infect. Dis. Clin. N. Am. 22: 361-376

Merten, H. A. and L. A. Durden 2000. A state-by-state survey of ticks recorded from humans in the United States. J. Vector Ecol. 25: 102-113

Moore, S. J. and M. Debboun 2007. History of insect repellents. Pp. 3-29. In M. Debboun, S. Frances, and D. Strickman [eds.] Insect repellents: principles, methods, and uses. CRC, Boca Raton, Fla.

Nentwig, G. 2003. Use of repellents as prophylactic agents. Parasitol. Res. 90: S40-S48.

Nicholson, W. L., D. E. Sonenshine, R. S. Lane and G. Uilenberg 2009. Ticks (Ixodida). In: Mullen G R, Durden L A (eds) Medical and Veterinary Entomology. Academic Press, Burlington, pp 493-542.

Robertson, S. E., B. P. Hull, O. Tomori, O. Bele, J. W. LeDuc and K. Esteves 1996. Yellow fever a decade of reemergence. JAMA 276: 1157-1162.

Salafsky, B., Y.-X. He, J. Li, T. Shibuya and K. Ramaswamy 2000. Study on the efficacy of a new long-acting formulation of N, N-diethyl-m-toluamide (DEET) for the prevention of tick attachment. J. Trop. Med. Hyg. 62: 169-172

SAS Institute 2000-2004. SAS 9.1.3 Help and documentation. Cary, N.C.

Schmidt, C. W. 2005. Outsmarting olfaction: the next generation of mosquito repellents. Env. Health Perspectives 113: A468-A471.

Schulze, T. L., R. A. Jordan, J. C. White, V. Roegner and S. P. Healy 2011. Geographical distribution and prevalence of selected *Borrelia*, *Ehrlichia*, and *Rickettsia* infections in *Amblyomma americanum* (Acari: Ixodidae) in New Jersey. J. Mosq. Control Assoc. 27: 236-244

Slaff, M., and C. S. Apperson 1989. A key to the mosquitoes of North Carolina and the Mid-Atlantic states. Agricultural Extension Service, North Carolina State University, Raleigh, N.C.

Sonenshine, D. E. 1993. Biology of ticks, vol 2. Oxford University Press, New York Strickman, D. 2007. PMD (p-menthane-3,8-diol) and Quwenling. pp. 347-351. In M. Debboun, S. Frances, and D. Strickman [eds.] Insect repellents: principles, methods, and uses. CRC, Boca Raton, Fla.

Thomas, G. D., I. L. Berry, D. R. Berkebile and S. R. Skoda. 1989. Comparison of three sampling methods for estimating adult stable fly (Diptera: Muscidae) populations. Environ. Entolmol. 18: 513-520.

United States Environmental Protection Agency. 2008. EPA Product Performance test guidelines, insect repellents to be applied to human skin.

United States Environmental Protection Agency. 2010. Product performance test guidelines, OPPTS 810.3700. Insect repellents to be applied to human skin.

Veltri, J. C., T. G. Osimitz, D. C. Bradford and B. C. Page 1994. Retrospective analysis to poison control centers resulting from exposure to N, N-diethyl-m-toluamide (DEET) from 1985-1989. Clinical Toxicol. 32: 1-16.

Xue, R-.D., A. Ali and J. F. Day 2007. Commercially available insect repellents and criteria for their use. pp. 405-415. In M. Debboun, S. Frances, and D. Strickman [eds.] Insect repellents: principles, methods, and uses. CRC, Boca Raton, Fla.

It is claimed:

1. A composition for controlling arthropods comprising effective amounts of geraniol, lauric acid, isopropyl myristate, mineral oil, and vitamin E;
   wherein said vitamin E is present in an amount of 0.1 to 2.5 weight percent, based on the total weight of the composition.

2. The composition of claim 1, further comprising triethyl citrate.

3. The composition of claim 2, further comprising vanillin.

4. The composition of claim 1, further comprising isopropyl alcohol.

5. The composition of claim 1, further comprising catnip oil.

6. The composition of claim 1, further comprising peppermint oil.

7. The composition of claim 1, further comprising cornmint oil.

8. A formulation for controlling arthropods comprising an effective amount of the composition of claim 1.

9. The formulation of claim 8, further comprising a carrier.

10. The formulation of claim 8, further comprising a surface-active agent.

11. The formulation of claim 8, further comprising a surfactant.

12. The formulation of claim 8, further comprising triethyl citrate and isopropyl alcohol.

13. The formulation of claim 8, further comprising butyl lactate, lanolin, sodium lauryl sulfate, isopropyl alcohol, glycerin and water.

14. The formulation of claim 8, wherein the composition is formulated in the form of one of a water-based formulation, a dust formulation, a spray formulation, or a burning formulation.

15. A method for controlling arthropods comprising the steps of:
- applying an effective amount of the formulation of claim 8 to a desired host, area, or object,
- wherein at least 1% of arthropods exposed to the applied formulation die.

16. A method for controlling arthropods comprising the steps of:
- applying an effective amount of the formulation of claim 8 to a desired host, area, or object,
- wherein at least 50% of arthropods exposed to the applied formulation are repelled from the host, area, or object.

17. A method for controlling arthropods comprising the steps of:
- applying an effective amount of the formulation of claim 8 to a desired host, area, or object,
- wherein at least 50% of arthropods exposed to the applied formulation display reduced motility.

* * * * *